(12) United States Patent
Shohat

(10) Patent No.: US 8,753,390 B2
(45) Date of Patent: Jun. 17, 2014

(54) METHODS FOR IMPLANTING A PROSTHESIS IN A HUMAN SHOULDER

(75) Inventor: Shaul Shohat, Kfar HaOranim (IL)

(73) Assignee: OrthoSpace Ltd., Caesarea (IL)

(*) Notice: Subject to any disclaimer, the term of this patent is extended or adjusted under 35 U.S.C. 154(b) by 722 days.

(21) Appl. No.: 12/531,332

(22) PCT Filed: Mar. 13, 2008

(86) PCT No.: PCT/IL2008/000347
§ 371 (c)(1),
(2), (4) Date: Sep. 15, 2009

(87) PCT Pub. No.: WO2008/111073
PCT Pub. Date: Sep. 18, 2008

(65) Prior Publication Data
US 2010/0023127 A1  Jan. 28, 2010

Related U.S. Application Data

(60) Provisional application No. 60/918,051, filed on Mar. 15, 2007.

(51) Int. Cl.
*A61F 2/02* (2006.01)
*A61F 2/08* (2006.01)

(52) U.S. Cl.
USPC .................................. 623/11.11; 623/14.12

(58) Field of Classification Search
USPC .......................................... 623/11.11, 14.12
See application file for complete search history.

(56) References Cited

U.S. PATENT DOCUMENTS

| 4,513,058 A | 4/1985 | Martin |
| 5,176,692 A | 1/1993 | Wilk et al. |
| 5,282,785 A | 2/1994 | Shapland et al. |
| 5,318,586 A | 6/1994 | Ereren et al. |
| 5,334,210 A | 8/1994 | Gianturco et al. |
| 5,336,252 A | 8/1994 | Cohen |
| 5,458,612 A | 10/1995 | Chin |
| 5,514,153 A | 5/1996 | Bonutti |

(Continued)

FOREIGN PATENT DOCUMENTS

| DE | 102007018341 | 10/2008 |
| DE | 102007051782 | 5/2009 |

(Continued)

OTHER PUBLICATIONS

Notice of Allowance Dated Mar. 14, 2012 From the US Patent and Trademark Office Re.: U.S. Appl. No. 11/630,257.

(Continued)

*Primary Examiner* — Dave Isabella
*Assistant Examiner* — Randy Shay
(74) *Attorney, Agent, or Firm* — Greenberg Traurig, LLP

(57) ABSTRACT

A prosthesis for reducing injury to soft tissues of the body, comprising an implantable member adapted to simulate at least one of a size or a shape of a naturally occurring bursa, where the member may be inflatable or otherwise expandable, flexible or rigid, and may be composed of a biocompatible, biodegradable, or non-biodegradable material. The member is adapted to be implanted at a musculoskeletal attachment site or at a site between a muscle and a bone, and is shaped and sized to reduce injury to the site. The prosthesis may also include a plug which seals the prosthesis automatically upon removal of an inflation tube.

26 Claims, 11 Drawing Sheets

(56) References Cited

U.S. PATENT DOCUMENTS

| | | | |
|---|---|---|---|
| 5,516,522 | A | 5/1996 | Peyman et al. |
| 5,641,505 | A | 6/1997 | Bowald et al. |
| 5,653,758 | A | 8/1997 | Daniels et al. |
| 5,720,762 | A | 2/1998 | Bass |
| 6,019,781 | A | 2/2000 | Worland |
| 6,102,928 | A | 8/2000 | Bonutti |
| 6,187,023 | B1 | 2/2001 | Bonutti |
| 6,248,131 | B1 | 6/2001 | Felt et al. |
| 6,527,693 | B2 | 3/2003 | Munro, III et al. |
| 6,746,465 | B2 | 6/2004 | Diederich et al. |
| 6,800,082 | B2 | 10/2004 | Rousseau |
| 6,932,834 | B2 | 8/2005 | Lizardi et al. |
| 7,144,398 | B2 | 12/2006 | Chern Lin et al. |
| 7,404,791 | B2 | 7/2008 | Linares et al. |
| 7,524,274 | B2 | 4/2009 | Patrick et al. |
| 7,601,113 | B2 | 10/2009 | Lebovic et al. |
| 7,632,291 | B2 | 12/2009 | Stephens et al. |
| 2001/0004710 | A1 | 6/2001 | Felt et al. |
| 2002/0016626 | A1 | 2/2002 | DiMatteo et al. |
| 2002/0052653 | A1* | 5/2002 | Durgin .................. 623/11.11 |
| 2002/0058947 | A1 | 5/2002 | Hochschuler et al. |
| 2003/0028196 | A1 | 2/2003 | Bonutti |
| 2003/0036728 | A1 | 2/2003 | Samson et al. |
| 2003/0078602 | A1 | 4/2003 | Rousseau |
| 2003/0105469 | A1 | 6/2003 | Karmon |
| 2003/0181939 | A1 | 9/2003 | Bonutti |
| 2004/0038874 | A1* | 2/2004 | Omoigui .................. 514/12 |
| 2004/0073107 | A1 | 4/2004 | Sioshansi et al. |
| 2004/0097794 | A1 | 5/2004 | Bonutti |
| 2004/0143285 | A1 | 7/2004 | Bonutti |
| 2004/0254625 | A1* | 12/2004 | Stephens et al. ........... 623/1.1 |
| 2004/0267315 | A1 | 12/2004 | Wolf et al. |
| 2005/0245938 | A1 | 11/2005 | Kochan |
| 2005/0273075 | A1 | 12/2005 | Krulevitch et al. |
| 2005/0278025 | A1 | 12/2005 | Ku et al. |
| 2006/0002967 | A1 | 1/2006 | Smestad et al. |
| 2006/0100629 | A1 | 5/2006 | Lee |
| 2006/0106361 | A1 | 5/2006 | Muni et al. |
| 2006/0147492 | A1 | 7/2006 | Hunter et al. |
| 2006/0149380 | A1 | 7/2006 | Lotz et al. |
| 2006/0182780 | A1 | 8/2006 | Riley |
| 2006/0233852 | A1 | 10/2006 | Milbocker |
| 2006/0241766 | A1 | 10/2006 | Felton et al. |
| 2007/0038292 | A1* | 2/2007 | Danielpour .................. 623/1.42 |
| 2007/0078477 | A1* | 4/2007 | Heneveld et al. ............ 606/191 |
| 2007/0118218 | A1 | 5/2007 | Hooper |
| 2007/0198022 | A1 | 8/2007 | Lang et al. |
| 2008/0033471 | A1 | 2/2008 | Paz et al. |
| 2008/0228025 | A1 | 9/2008 | Quick |
| 2008/0269897 | A1 | 10/2008 | Joshi et al. |
| 2009/0048683 | A1 | 2/2009 | Morris et al. |
| 2009/0112214 | A1 | 4/2009 | Philippon et al. |
| 2009/0187252 | A1 | 7/2009 | Howald et al. |
| 2009/0312807 | A1 | 12/2009 | Boudreault et al. |
| 2010/0069947 | A1 | 3/2010 | Sholev et al. |
| 2010/0191332 | A1 | 7/2010 | Euteneuer et al. |
| 2011/0295226 | A1 | 12/2011 | Shohat et al. |
| 2014/0074245 | A1 | 3/2014 | Shohat et al. |

FOREIGN PATENT DOCUMENTS

| | | |
|---|---|---|
| EP | 0507645 | 10/1992 |
| JP | 06-510450 | 11/1994 |
| JP | 10-504202 | 4/1998 |
| JP | 2003-325685 | 11/2003 |
| JP | 2006-247257 | 9/2006 |
| WO | WO 93/04727 | 3/1993 |
| WO | WO 95/33502 | 12/1995 |
| WO | WO 2005/105172 | 11/2005 |
| WO | WO 2006/001009 | 1/2006 |
| WO | WO 2006/055516 | 5/2006 |
| WO | WO 2006/074879 | 7/2006 |
| WO | WO 2007/002561 | 1/2007 |
| WO | WO 2007/054934 | 5/2007 |
| WO | WO 2007/125060 | 11/2007 |
| WO | WO 2008/111073 | 9/2008 |
| WO | WO 2008/111078 | 9/2008 |
| WO | WO 2008/139473 | 11/2008 |
| WO | WO 2008/157727 | 12/2008 |
| WO | WO 2012/017438 | 2/2012 |

OTHER PUBLICATIONS

Invitation to Pay Additional Fees Dated Sep. 17, 2008 From the International Searching Authority Re.: Application No. PCT/IL08/00354.

Preliminary International Preminary Report on Patentability Dated Oct. 22, 2009 From the International Bureau of WIPO Re.: Application No. PCT/IL2008/000354.

International Search Report Dated Nov. 20, 2008 From the International Searching Authority Re.: Application No. PCT/IL08/00347.

International Search Report Dated Nov. 26, 2008 From the International Searching Authority Re.: Application No. PCT/IL08/00354.

Invitation to Pay Additional Fees Dated Sep. 23, 2008 From the International Searching Authority Re.: Application No. PCT/IL08/00347.

Patentability Search on Expandable Prostheses Particularly Useful for Rotator Cuff Protection Dated Oct. 31, 2007 Effectuated by Sol Scheinbein.

Written Opinion Dated Nov. 20, 2008 From the International Searching Authority Re.: Application No. PCT/IL08/00347.

Written Opinion Dated Nov. 26, 2008 From the International Searching Authority Re.: Application No. PCT/IL08/00354.

International Preliminary Report on Patentability Dated Jan. 21, 2010 From the International Bureau of WIPO Re.: Application No. PCT/IL2008/000347.

Translation of Office Action Dated Mar. 28, 2012 From the State Intellectual Property Office of the People's Republic of China Re. Application No. 200880014369.0.

Translation of Office Action Dated Feb. 17, 2012 From the State Intellectual Property Office of the People's Republic of China Re. Application No. 200880015430.3.

Translation of Office Action Dated Mar. 30, 2012 From the State Intellectual Property Office of the People's Republic of China Re. Application No. 200880024447.5.

Supplementary European Search Report and the European Search Opinion Dated Jun. 6, 2011 From the European Patent Office Re. Application No. 08738353.5.

Translation of Notice of Payment of the Restoration Fee for Unity of Invention Dated Jul. 26, 2011 From the State Intellectual Property Office of the People's Republic of China Re. Application No. 200880014369.0.

Translation of Notice of Reason for Rejection Dated Nov. 5, 2010 From the Japanese Patent Office Re. Application No. 2007-517651.

Communication Pursuant to Article 94(3) EPC Dated Dec. 1, 2011 From the European Patent Office Re. Application No. 05754685.5.

Translation of Office Action Dated Oct. 19, 2011 From the State Intellectual Property Office of the People's Republic of China Re. Application No. 200880014369.0.

Communication Pursuant to Article 94(3) EPC Dated Feb. 16, 2012 From the European Patent Office Re. Application No. 08738353.5.

Response Dated Dec. 30, 2011 to the Communication Pursuant to Rules 70(2) and 70a(2) EPC of Jun. 24, 2011 From the European Patent Office Re. Application No. 08738353.5.

Response Dated Dec. 28, 2011 to Supplementary European Search Report and the European Search Opinion of Jun. 6, 2011 From the European Patent Office Re. Application No. 08738353.5.

Response Dated Feb. 27, 2011 to Office Action of Oct. 27, 2009 From the Israel Patent Office Re.: Application No. 180270.

International Preliminary Report on Patentability Dated Jan. 21, 2010 From the International Bureau of WIPO Re.: Application No. PCT/IL2008/000662.

International Search Report and the Written Opinion Dated Oct. 23, 2008 From the International Searching Authority Re.: Application No. PCT/IL08/00662.

Official Action Dated Apr. 14, 2010 From the US Patent and Trademark Office Re.: U.S. Appl. No. 11/630,257.

(56) References Cited

OTHER PUBLICATIONS

Communication Relating to the Results of the Partial International Search Dated Nov. 3, 2011 From the International Searching Authority Re. Application No. PCT/IL2011/000637.
International Search Report and the Written Opinion Dated Jan. 9, 2012 From the International Searching Authority Re. Application No. PCT/IL2011/000637.
Notification of Publication of Patent Application for Invention and Entering the Substantive Examination Proceeding Dated Jul. 28, 2010 From the Patent Office of the People's Rebublic of China Re. Application No. 200880024447.5 and Its Translation Into English.
Response Dated Oct. 20, 2010 to Notification of Publication of Patent Application for invention and Entering the Substantive Examination Proceeding of Jul. 28, 2010 From the Patent Office of the People's Rebublic of China Re. Application No. 200880024447.5.
Notification of Publication of Patent Application for Invention and Entering the Substantive Examination Proceeding Dated Oct. 13, 2010 From the Patent Office of the People's Republic of China Re. Application No. 200880015430.3.
Response Dated Jan. 6, 2011 to Notification of Publication of Patent Application for Invention and Entering the Substantive Examination Proceeding Dated Oct. 13, 2010 From the Patent Office of the People's Republic of China Re. Application No. 200880015430.3.
Translation of Office Action Dated Jan. 11, 2011 From the State Intellectual Property Office of the People's Republic of China Re. Application No. 200580028684.5.
International Preliminary Report on Patentability Dated Jul. 27, 2006 From the International Preliminary Examining Authority Re.: Application No. PCT/IL2005/000672.
Translation of Office Action Dated Oct. 31, 2008 From the State Intellectual Property Office of the People's Republic of China Re.: Application No. 200580028684.5.
Communication Relating to the Results of the Partial International Search Dated Nov. 18, 2005 From the International Searching Authority Re.: Application No. PCT/IL2005/000672.
International Search Report Dated Feb. 22, 2006 From the International Searching Authority Re.: Application No. PCT/IL2005/000672.
Office Action Dated Oct. 27, 2009 From the Israel Patent Office Re.: Application No. 180270 and Its Translation Into English.
Official Action Dated Jun. 8, 2009 From the US Patent and Trademark Office Re.: U.S. Appl. No. 11/630,257.
Official Action Dated Aug. 19, 2009 From the US Patent and Trademark Office Re.: U.S. Appl. No. 11/630,257.
Response Dated Jan. 4, 2010 to Decision of Rejection of Oct. 16, 2009 From the State Intellectual Property Office of the People's Republic of China Re.: Application No. 200580028684.5.
Response Dated Dec. 22, 2009 to Official Action of Aug. 19, 2009 From the US Patent and Trademark Office Re.: U.S. Appl. No. 11/630,257.
Translation of Decision on Rejection Dated Oct. 16, 2009 From the State Intellectual Property Office of the People's Republic of China Re.: Application No. 200580028684.5.
Translation of Office Action Dated Jul. 3, 2009 From the State Intellectual Property Office of the People's Republic of China Re.: Application No. 200580028684.5.
Written Opinion Dated Feb. 22, 2006 From the International Searching Authority Re.: Application No. PCT/IL2005/000672.
Examiner's Report Dated Apr. 28, 2010 From the Australian Government, IP Australia Re. Application No. 2005257050.
Translation of Official Copy of Decision of Rejection Dated Jun. 7, 2011 From the Japanese Patent Office Re. Application No. 2007-517651.
Response Dated Apr. 21, 2011 to Notice of Reason for Rejection of Nov. 5, 2010 From the Japanese Patent Office Re. Application No. 2007-517651.
Communication Pursuant to Rules 70(2) and 70a(2) EPC Dated May 24, 2011 From the European Patent Office Re. Application No. 08738353.5.
Response Dated May 12, 2011 to Office Action of Jan. 11, 2011 From the State Intellectual Property Office of the People's Republic of China Re. Application No. 200580028684.5.
Request for Reconsideration Filed With an RCE Dated Aug. 9, 2010 to Official Action of Apr. 14, 2010 From the US Patent and Trademark Office Re.: U.S. Appl. No. 11/630,257.
Restriction Official Action Dated Feb. 6, 2012 From the US Patent and Trademark Office Re. U.S. Appl. No. 12/531,073.
Restriction Official Action Dated Dec. 12, 2011 From the US Patent and Trademark Office Re. U.S. Appl. No. 12/531,073.
Patent Examination Report Dated Jul. 13, 2012 From the Australian Government, IP Australia Re. Application No. 2008224435.
Communication Pursuant to Article 94(3) EPC Dated Dec. 21, 2012 From the European Patent Office Re. Application No. 08738353.5.
Office Action Dated Jun. 10, 2013 From the Israel Patent Office Re. Application No. 200939 and Its Translation into English.
Office Action Dated Nov. 18, 2012 from the Israel Patent Office Re. Application No. 180270 and Its Translation into English.
Office Action Dated Nov. 20, 2012 from the Israel Patent Office Re. Application No. 200939 and Its Translation into English.
Official Action Dated Jul. 19, 2013 From the US Patent and Trademark Office Re. U.S. Appl. No. 13/811,069.
Restriction Official Action Dated Sep. 24, 2012 From the US Patent and Trademark Office Re. U.S. Appl. No. 12/764,238.
Translation of Notice of Reason for Rejection Dated Nov. 27, 2012 From the Japanese Patent Office Re. Application No. 2009-553278.
Translation of Office Action Dated Dec. 11, 2012 From the State Intellectual Property Office of the People's Republic of China Re. Application No. 200880015430.3.
Office Action Dated Oct. 30, 2013 From the Israel Patent Office Re. Application No. 200939 and Its Translation Into English.
Patent Examination Report Dated Aug. 29, 2013 From the Australian Government, IP Australia Re. Application No. 2008224435.
Translation of Office Action dated Jul. 11, 2013 from the State Intellectual Property Office of the People's Republic of China Re. Application No. 20088015430.3
Translation of Search Report dated Jul. 11, 2013 from the State Intellectual Property Office of the People's Republic of China Re. Application No. 20088015430.3
Supplementary European Search Report and the European Search Opinion dated May 6, 2013 from the European Patent Office Re. Application No. 08719972.5.
Notice of Reason for Rejection Dated Mar. 14, 2014 From the Japanese Patent Office Re. Application No. 2013-99793 and Its Translation Into English.
Office Action Dated Feb. 26, 2014 From the Israel Patent Office Re. Application No. 200939 and Its Translation Into English.
Office Action Dated Jan. 28, 2014 From the State Intellectual Property Office of the People's Republic of China Re. Application No. 200880015430.3.

\* cited by examiner

METHODS FOR IMPLANTING A PROSTHESIS IN A HUMAN SHOULDER

RELATED APPLICATIONS

This application is a National Phase of PCT Patent Application No. PCT/IL2008/000347 having International filing date of Mar. 13, 2008 which claims the benefit under 35 USC 119(e) of U.S. Provisional Patent Application No. 60/918,051, filed on Mar. 15, 2007, the disclosure of which is herein incorporated by reference.

FIELD OF INVENTION

The present inventions relate generally to the field of medical devices and the treatment of human medical conditions using the medical devices. More specifically, the present inventions include expandable prosthetic devices used for treating a variety of conditions, including rotator cuff injuries, broken and/or depressed bone fractures, infection and/or inflammation in the body.

BACKGROUND OF THE INVENTION

Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues.

Other bodily injuries, such as fractures of hollow bones (i.e. having medullar cavities) and depression fractures of vertebra require complex procedures for treatment, for example alignment and fixation of multiple bone fragments for the former and disc replacement for the latter.

Various solutions to problems in treatment of these injuries have been proposed, for example:

U.S. Pat. App. Pub. No. 2007/0198022 to Lang, et al., the disclosure of which is incorporated herein by reference, describes methods, compositions and tools for repairing articular surfaces repair materials and for repairing an articular surface. The articular surface repairs are customizable or highly selectable by patient and geared toward providing optimal fit and function. The surgical tools are designed to be customizable or highly selectable by patient to increase the speed, accuracy and simplicity of performing total or partial arthroplasty.

JP Pat. App. Pub. No. 2006-247257 to Yasuhiko, et al., the disclosure of which is incorporated herein by reference, describes a bone cement injector which is equipped with an injection tube and a balloon detachably mounted on one end of the injection tube, where the balloon is formed with a bioabsorptive material. Using the bone cement injector of this invention, the balloon is inserted into the damaged section of the vertebra to be treated, and subsequently the bone cement is injected into this balloon. Thereby, the bone cement can be injected into the corpus vertebra of the damaged part of the vertebra while preventing the blood from mixing in the bone cement and the bone cement from leaking into the vertebral canal.

U.S. Pat. App. Pub. No. 2005/0245938 to Kochan, the disclosure of which is incorporated herein by reference, describes a device for repair of intervertebral discs and cartilages in articular joints includes a catheter for inserting through a cannula, the catheter having a distal end and a proximal end and a lumen extending longitudinally therethrough. An expandable balloon may optionally be detachably attached to the catheter near the distal end. The proximal end of the catheter is coupled to an injector that holds a supply of a thermoplastic elastomer material at a predetermined elevated temperature sufficiently high to maintain the thermoplastic elastomer at a liquid state. The device allows a thermoplastic elastomer material to be injected into the intervertegral disc space or the articular joint space as a replacement prosthetic for the disc's nucleus pulposus or the joint's cartilage. This procedure is carried out percutaneously through the cannula.

U.S. Pat. No. 6,755,862 to Keynan, the disclosure of which is incorporated herein by reference, describes an intramedullary support strut for a long bone for a range of different applications including anchoring and fixation. The strut is in the form of nested telescopic members. In the retracted configuration, the strut is compact and may be inserted into position aligned with a shaft made in the medullary canal via a portal made in the lateral cortex of the bone. The strut may then be telescopically extended into the medullary canal to provide the required support.

U.S. Pat. No. 6,613,052 to Kinnett, the disclosure of which is incorporated herein by reference, describes an apparatus developed to enable a surgeon to perform multiple orthopedic surgical operations, such as orthopedic surgical resectioning, total joint replacement and fixation of fractures, based on a single reference point. The apparatus is adjustable to conform to the needs and dimensions of individual patients and the surgical procedure(s) to be performed. The apparatus includes a support adapted for insertion into and alignment within the medullary cavity of a patient's bone. The support is capable of expanding into the bone so that the support is fixed within the bone and alignable to the bone. The support may be implanted to align a fractured bone, or extend a distance beyond its fixed position within the medullary cavity to provide a known surgical reference point. The apparatus includes one or more cutting guides mountable on the support and used in performing the desired surgical procedure(s). The cutting guides are positionable with respect to the known surgical reference point created by the support which enables the user to accurately position and secure various instruments at the desired position about the patient's anatomy.

SUMMARY OF THE INVENTION

An aspect of some embodiments of the invention relates to prostheses adapted to reduce injuries between soft tissues of the body and other tissues. In an embodiment of the invention, soft tissues are for example, tendons and/or ligaments. In an embodiment of the invention, other tissues are, for example, bones. In an embodiment of the invention, the prosthesis is expandable. Optionally, the prosthesis is elastic. In some embodiments of the invention, the prosthesis is rigid. In an embodiment of the invention, the prosthesis is shaped and/or sized to simulate a bursa naturally occurring in the body. Optionally, the bursa simulated is the one expected to be present at the implantation site of the prosthesis in a healthy patient.

In an embodiment of the invention, an expandable prosthesis adapted to reduce and/or eliminate injury to the rotator cuff. Optionally, the expandable prosthesis is sponge-like. Optionally, the expandable prosthesis is inflatable. In some exemplary embodiments of the invention, the expandable prosthesis is adapted to be inserted between the tendons of the rotator cuff and the acromion and/or coracoid process. Expandable prosthesis is biocompatible and/or biodegradable, in an exemplary embodiment of the invention. Optionally, the expandable prosthesis is adapted to elute pharmaceutical agents once implanted in a patient's body. In an embodiment of the invention, inflatable expandable prosthesis is inflated with filler, for example a gas, liquid, and/or gel. Optionally, the filler is biocompatible and/or biodegradable. In some embodiments of the invention, the prosthesis is only partially filled.

In some embodiments of the invention, the prosthesis is provided with anchoring devices adapted to maintain the prosthesis in a steady relationship with the anatomical features around the implantation site. Optionally, the prosthesis is contoured along its exterior to accommodate anatomical features around the implantation site.

An aspect of some embodiments of the invention relates to a method for implanting an expandable prosthesis adapted to reduce and/or eliminate injury between soft tissues of the body and other tissues, for example to the rotator cuff. In an embodiment of the invention, the expandable prosthesis is either sponge-like or inflatable and is expanded in a space between the tendons of the rotator cuff and the acromion and/or coracoid process. In some embodiments of the invention, a prosthesis implantation and/or inflation device is used to implant and/or inflate the expandable prosthesis.

An aspect of some embodiments of the invention relates to an expandable prosthesis for the alignment of bone fragments which is provided with walls thick enough to withstand the stresses of normal activity while still maintaining the bone fragments in alignment. In an embodiment of the invention, the expandable prosthesis is inflatable. In some exemplary embodiments of the invention, the expandable prosthesis is adapted to be inserted into the medullar cavity of a plurality of bone fragments. Expandable prosthesis is biocompatible and/or biodegradable, in an exemplary embodiment of the invention. Optionally, the expandable prosthesis is adapted to elute pharmaceutical agents once implanted in a patient's body. In an embodiment of the invention, inflatable expandable prosthesis is inflated with filler, for example a gas, liquid, cement and/or gel, to provide sufficient rigidity to expandable prosthesis to align a plurality of bone fragments. Optionally, the filler is biocompatible and/or biodegradable.

In some embodiments of the invention, the prosthesis is provided with a calibration kit which is designed to determine the size and/or shape of the medullar cavity of the bone fragments and/or to choose an appropriate sized prosthesis for implantation into the cavity.

An aspect of some embodiments of the invention relates to a method for aligning bone fragments using an inflatable, expandable prosthesis. In an embodiment of the invention, an inflatable, expandable prosthesis is introduced into the medullar channel of a plurality of bone fragments. In some embodiments of the invention, a prosthesis implantation and/or inflation device is used to implant and/or inflate the expandable prosthesis. Optionally, pharmaceutical agents are eluted into the patient by the expandable prosthesis.

An aspect of some embodiments of the invention relates to an expandable prosthesis for treating inflammation and/or infection. Optionally, the expandable prosthesis is a sponge-like structure, sponge-like being defined as including at least one of the following properties: porous, absorbent and/or compressible. Optionally, the expandable prosthesis is inflatable. Expandable prosthesis is biocompatible and/or biodegradable, in an exemplary embodiment of the invention. Optionally, the expandable prosthesis is adapted to elute pharmaceutical agents once implanted in a patient's body. Expandable sponge-like device optionally contains within its cavities at least one biocompatible and/or biodegradable gelling material that expands when it comes into contact with at least one bodily fluid, for example by absorbing water.

In an embodiment of the invention, inflatable expandable prosthesis is inflated with filler, for example a gas, liquid, and/or gel. Optionally, the filler is biocompatible and/or biodegradable and/or contains the pharmaceutical agents. In some embodiments, elution of pharmaceutical agents is according to a schedule timed with the biodegradable properties of the expandable prosthesis.

An aspect of some embodiments of the invention, relates to an expandable prosthesis for treating depressed fractures. In some embodiments of the invention, the expandable prosthesis comprises an inner section and an external section. Optionally, at least one section of the expandable prosthesis is sponge-like. The at least one sponge-like section optionally contains within its cavities at least one biocompatible and/or biodegradable gelling material that expands when it comes into contact with at least one bodily fluid, for example by absorbing water. Optionally, at least one section of the expandable prosthesis is inflatable. In an embodiment of the invention, the at least one inflatable expandable section is inflated with filler, for example a gas, liquid, cement and/or gel, to provide sufficient rigidity to treat the depressed fracture.

In some exemplary embodiments of the invention, the expandable prosthesis is adapted to be inserted at or near a fractured vertebra. Expandable prosthesis is optionally biocompatible and/or biodegradable, in an exemplary embodiment of the invention. Optionally, the expandable prosthesis is adapted to elute pharmaceutical agents once implanted in a patient's body.

In an embodiment of the invention, at least one section of the prosthesis is inflated with filler, for example a gas, liquid, cement and/or gel. Optionally, the filler is biocompatible and/or biodegradable. In some embodiments of the invention, the expandable prosthesis is adapted to have at least one section removed prior to closing the patient. In an embodiment of the invention, at least one section is adapted to withstand the expected pressures from being implanted at or near a vertebra of the patient. In an embodiment of the invention, the expandable prosthesis is inflated and/or implanted using a plurality of prosthesis inflation and/or implantation devices.

An aspect of some embodiments of the invention relates to a method for treating depressed fractures using an expandable prosthesis. In an embodiment of the invention, the method implants at least one section of an expandable prosthesis comprising a plurality of separately expandable and/or retractable sections. In an embodiment of the invention, at least one section of an expandable prosthesis is used to properly deploy filler for treating the depressed fracture. Optionally, at least one section of the expandable prosthesis is withdrawn from the patient before closing the patient. Optionally, at least one section of the expandable prosthesis is sealed and implanted in the patient. In some embodiments of the invention, pharmaceutical agents are eluted into the patient by the expandable prosthesis.

An aspect of some embodiments of the invention relates to a prosthesis implantation and/or inflation device. In an embodiment of the invention, the prosthesis implantation and/or inflation device includes a syringe adapted to inject filler into an expandable prosthesis, for example through a tube which operatively connects syringe to the expandable prosthesis. In some embodiments of the invention, the syringe is comprised of at least a plunger and a canister. Optionally, the plunger is advanced through the canister by the device in order to inject filler into the prosthesis. Optionally, the canister is advanced against the plunger, which remains relatively fixed due to counterforce from a backstop, in order to inject filler into the prosthesis.

In some exemplary embodiments of the invention, the prosthesis implantation and/or inflation device includes a safety. Optionally, the safety comprises at least a spring and a ball, wherein the ball acts as a counterpart to a groove in the backstop. Excessive force on the backstop by continued advancement of the canister towards the plunger triggers the safety, popping the ball out of the groove and freeing the backstop to move. In an embodiment of the invention, the placement of the backstop is according to a predetermined level of desired inflation of the prosthesis.

There is thus provided in accordance with an embodiment of the invention, a prosthesis for reducing injury to soft tissues of the body, comprising: a member adapted to simulate at least one of a size or a shape of a naturally occurring bursa.

In an embodiment of the invention, the member is expandable. Optionally, the member is adapted to be at least partially inflated. Optionally, the member is inflated sufficiently to reduce rubbing of the soft tissues against other tissues while permitting at least some movement of the soft tissues relative to the other tissues. Optionally, at least some movement of the soft tissues relative to the other tissues is full movement. In an embodiment of the invention, the member is sponge-like. Optionally, the sponge-like member is provided with a fluid absorbent material which when fluids are absorbed induces expansion of the sponge-like expandable member.

In an embodiment of the invention, the prosthesis is constructed of at least one of a biocompatible or biodegradable material. Optionally, the at least one of a biocompatible or biodegradable material is PCL, PGA, PHB, plastarch material, PEEK, zein, PLA, PDO, PLGA, collagen or methyl cellulose.

In an embodiment of the invention, the prosthesis is constructed of at least one non-biodegradable material. Optionally, the at least one non-biodegradable material is polyethylene, polyurethane, silicon, or poly-paraphenylene terephthalamide.

In an embodiment of the invention, the prosthesis further comprises a rigid ring having a lumen therein attached to the member, wherein the lumen provides fluid communication to an inner space of the member.

In an embodiment of the invention, the prosthesis further comprises a plug adapted to lodge in the lumen thereby sealing the inner space of the member. Optionally, the plug is constructed of at least one of a biocompatible or biodegradable material.

In an embodiment of the invention, the member is elastic.

In an embodiment of the invention, the prosthesis further comprises at least one anchoring device for stabilizing the prosthesis upon implantation. Optionally, the at least one anchoring device is constructed of at least one of a biocompatible or biodegradable material.

In an embodiment of the invention, the member is contoured to act as a counterpart to natural anatomical features of an implantation site.

In an embodiment of the invention, adapted to elute at least one pharmaceutical agent.

In an embodiment of the invention, the size of the prosthesis is approximately 2 cm to 10 cm in length along a long axis, approximately 2 cm to 7 cm in length along a short axis and approximately 0.5 mm to 20 mm in height, when expanded.

In an embodiment of the invention, the member is rigid. Optionally, the member is contoured to act as a counterpart to natural anatomical features of an implantation site while permitting at least some movement of the soft tissues relative to other tissues.

In an embodiment of the invention, adapted for reducing injury to a rotator cuff. In an embodiment of the invention, adapted for reducing injury to at least one of a flexor or an extensor. In an embodiment of the invention, adapted for reducing injury between a quadriceps and a femur. In an embodiment of the invention, adapted for reducing injury between a skin and a plantar fascia and a calcaneus of the body. In an embodiment of the invention, injury is at least one of inflammation or infection.

There is further provided in accordance with an exemplary embodiment of the invention, a method for implanting a prosthesis adapted to reduce injury to between soft tissues and other tissues of a body, comprising: placing the prosthesis into an implantation site between the soft tissues and the other tissues; and, simulating with the prosthesis a bursa naturally occurring at the implantation site. In an embodiment of the invention, the method further comprises eluting at least one pharmaceutical agent from the prosthesis at the implantation site. Optionally, placing and simulating occurs without significantly reducing movement of the soft tissues relative to the other tissues. Optionally, the soft tissues are tendons of a rotator cuff and the other tissues are at least one of a humerus, an acromion or a coracoid process.

There is further provided in accordance with an exemplary embodiment of the invention, a prosthesis for the alignment of bone fragments, comprising: a member adapted to be implanted in the medullar cavity of the bone fragments, wherein the member is provided with an outer wall thickness adapted to accommodate at least a minimum level of rigidity necessary to maintain bone fragment alignment during normal activity. In an embodiment of the invention, the prosthesis further comprises a calibration kit adapted to perform at least one of determining the size of the medullar cavity or introducing the proper sized member into the medullar cavity. Optionally, the member is tubular or vasiform in shape. Optionally, at least the member is constructed of at least one of a biocompatible or biodegradable material. Optionally, the member has an approximate outer diameter between 2 mm and 15 mm and an approximate length between 5 cm and 50 cm. Optionally, the prosthesis is adapted to elute at least one pharmaceutical agent.

There is further provided in accordance with an exemplary embodiment of the invention, a method for aligning bone fragments, comprising: introducing a prosthesis into the medullar cavity of a plurality of bone fragments; and, inflating the prosthesis to a sufficient rigidity to hold the bone fragments in alignment during normal activity. In an embodiment of the invention, the method further comprises determining the size of the medullar cavity using a calibration kit.

There is further provided in accordance with an exemplary embodiment of the invention, a prosthesis adapted for treating depressed fractures comprising a plurality of separately expandable and retractable sections. Optionally, the prosthesis comprises an inner section and an outer section, wherein the outer section at least partially surrounds the inner section. Optionally, the inner section is cylindrical and measures approximately 2 cm to 7 cm in diameter and 2 cm to 5 cm in height. Optionally, the inner section and outer section are manufactured from at least one of polyurethane, ultra high molecular weight polyethylene, poly-paraphenylene terephthalamide, PCL, PGA, PHB, plastarch material, PEEK, zein, PLA, PDO and PLGA, collagen, or methyl cellulose.

There is further provided in accordance with an exemplary embodiment of the invention, a method for treating a depressed fracture using a prosthesis comprising a plurality of separately expandable and retractable sections, comprising: introducing the prosthesis to the implantation area, wherein the fracture is concave in relation to the area; inflating an inner section; inflating an outer section; deflating the inner section; and, filling a cavity left by the deflating of the inner section such that support is rendered to the depressed fracture from the filled cavity. Optionally, the inner section is withdrawn prior to filling the cavity.

In an embodiment of the invention, the method further comprises withdrawing the outer section after filling the cavity.

There is further provided in accordance with an exemplary embodiment of the invention, a system for sealing an inflatable prosthesis, comprising: a prosthesis inflation device; a tube operatively connected to the prosthesis near one end and the prosthesis inflation device on the other end; a plug attached to the tube at the prosthesis end of the tube; and, a rigid ring attached to the prosthesis and slidably attached around the tube between the prosthesis inflation device and the plug; wherein pulling the tube towards the prosthesis inflation device causes plug to lodge in the rigid ring, sealing the prosthesis with the plug. Optionally, the plug is attached to the tube by gripping protrusions.

There is further provided in accordance with an exemplary embodiment of the invention, a method of sealing an inflatable prosthesis, comprising: pulling a tube out of the prosthesis and through a rigid ring; and, lodging a plug located on the end of the tube in the rigid ring.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

As described above, repeated strenuous motion often causes sensitive soft tissues to suffer wear and tear injuries from repeatedly rubbing against one another and/or hard tissues, such as bone. Tears of tendons and/or ligaments and articular capsule disintegration are examples of this type of injury. In addition, these tissues can be adversely affected by inflammation, infection, disease and/or genetic predispositions which lead to degeneration of these tissues.

Injuries to soft tissues such as tendons can cause pain and impaired function of the area served by the tendon. Typically, a bursa can be found near areas where "friction" injuries due to the rubbing are prone to occur. A bursa is a natural fluid collection that permits movements between tendons and/or ligaments and bone parts and prevents injury to these tendons by acting as a cushion and/or movement facilitator between them.

In some embodiments of the invention, prostheses described herein are shaped and/or sized to simulate the natural bursa found in the intended area of implantation. For example, in some of the rotator cuff embodiments described below, the described exemplary prostheses are shaped and/or sized to simulate the subacromial bursa. Optionally, the prostheses are sized to supplement a natural bursa which is misshapen and/or undersized, bringing the combination of the natural bursa and the prosthesis into line with the shape and/or size of a healthy bursa.

The rotator cuff is an anatomical term given to the group of muscles and their tendons that act to stabilize the shoulder and to permit rotation and abduction of the arm. Along with the teres major and the deltoid, the four muscles of the rotator cuff make up the six muscles of the human body which connect to the humerus and scapula. Injury to the tendons and/or these muscles can cause pain and impaired function of the shoulder. The subacromial bursa is a natural fluid collection that permits movement of these rotator cuff tendons beneath the acromion and coracoid process, both of which are part of scapula bone. In some rotator cuff injuries, the subacromial bursa becomes inflamed and suffers from a reduced ability to prevent injury to the tendons through friction.

Figure 1:
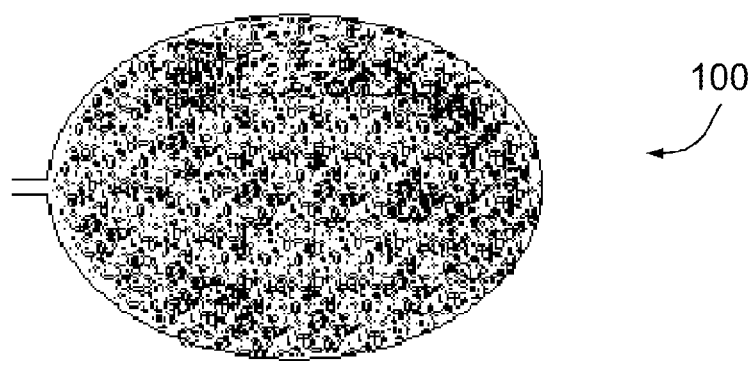
FIG. 1 is an illustration of a sponge-like expandable prosthesis adapted to reduce and/or eliminate injury to the rotator cuff, in accordance with an exemplary embodiment of the invention.

Referring to FIG. 1, an expandable prosthesis 100 is shown which is adapted to reduce and/or eliminate injury to the rotator cuff, in an exemplary embodiment of the invention. In an exemplary embodiment of the invention, expandable prosthesis 100 is introduced between the above mentioned acromion and coracoid processes and the rotator cuff tendons to prevent continued injury to these body parts and/or to permit relatively unhindered (relative to the movement afforded to the shoulder without treatment) or free shoulder movement, shown and described in more detail with respect to FIG. 3. In some embodiments of the invention, expandable prosthesis 100 comprises an expandable member which is a sponge-like structure. It should also be understood that sponge-like expandable prosthesis 100 is adapted to elute pharmacological substances such as anti-inflammatory and/or antibiotic and/or pro-angiogenesis substances, in some exemplary embodiments of the invention.

In an exemplary embodiment of the invention, sponge-like expandable prosthesis 100 is biodegradable and/or biocompatible. The sponge-like structure is manufactured from at least one biodegradable and/or biocompatible synthetic material such as, but not limited to, polycaprolactone ("PCL"), polyglycolide ("PGA"), polyhydroxybutyrate ("PHB"), plastarch material, polyetheretherketone ("PEEK"), zein, polylactic acid ("PLA"), polydioxanone ("PDO") and poly(lactic-co-glycolic acid) ("PLGA"), or any combination and/or family members thereof. In some exemplary embodiments of the invention, the sponge-like structure is manufactured from at least one "naturally-derived" biodegradable and/or biocompatible materials such as collagen and/or methyl cellulose. In an exemplary embodiment of the invention, sponge-like expandable prosthesis 100 is imparted expandable properties, at least in part, by placing within its cavities at least one biocompatible and/or biodegradable material which expands after coming into contact with fluids. Optionally, the fluids are bodily fluids. Optionally, the at least one biocompatible and/or biodegradable material is a gel.

In some exemplary embodiments of the invention, sponge-like expandable prosthesis 100 is non-biodegradable. Non-biodegradable expandable prostheses are manufactured of biocompatible materials such as polyethylene, Kevlar® (poly-paraphenylene terephthalamide), polyurethane or silicon, or any combination thereof, in some embodiments of the invention. In some exemplary embodiments of the invention, the expandable prosthesis is manufactured from biologically derived, biocompatible and/or biodegradable materials such as collagen. In an exemplary embodiment of the invention, prosthesis 100, when expanded, has approximately the same dimensions as other prostheses when expanded, described below.

Figure 2:
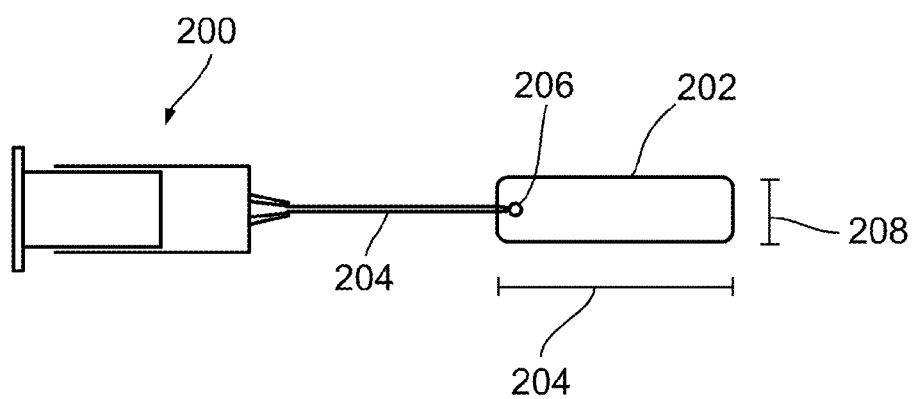
FIG. 2 is a cutaway view of a portion of a prosthesis implantation and/or inflation device and an inflatable expandable prosthesis adapted to reduce and/or eliminate injury to the rotator cuff, in accordance with an exemplary embodiment of the invention.

Referring to FIG. 2, a cutaway view of a portion of a prosthesis implantation and/or inflation device 200 and a prosthesis 202 with an expandable member which is inflatable is shown, in accordance with an exemplary embodiment of the invention. Exemplary embodiments of prosthesis implantation and/or inflation device 200 are described in more detail with respect to FIGS. 16-17. In an exemplary embodiment of the invention, inflatable expandable prosthesis 202 is introduced between the above mentioned acromion and coracoid processes and the rotator cuff tendons to prevent continued injury to these body parts and/or to permit relatively unhindered or free shoulder movement, shown and described in more detail with respect to FIG. 3. Optionally, alternatively and/or additionally, an expandable prosthesis comprises an inflatable structure and a sponge-like structure in combination.

In an exemplary embodiment of the invention, inflatable expandable prosthesis 202 is rectangular shaped when deflated and resembles a cuboid parallelepiped when inflated. In an exemplary embodiment of the invention, inflatable expandable prosthesis 202 is circular or oval in shape when deflated and when inflated resembles a cylindrical disc or ovoid. It should be understood, however, that many shapes could be adapted to be implanted between the acromion and coracoid processes and the rotator cuff tendons to prevent at least some injury to the rotator cuff and/or to permit relatively unhindered or free shoulder movement for a patient, in an exemplary embodiment of the invention. In some embodiments of the invention, prosthesis 202 is adapted to be inserted deflated into a patient's body through a cannula. Optionally, the cannula is a 5 mm-7 mm cannula. In an embodiment of the invention, a long axis 204 (x-axis) of inflatable expandable prosthesis 202 is approximately 2 cm to 10 cm in length when inflated. In some embodiments of the invention, a short axis 208 (y-axis) of inflatable expandable prosthesis 202 is approximately 2 cm to 7 cm in length when inflated In some exemplary embodiments of the invention, inflatable expandable prosthesis 202 is 0.5 mm to 20 mm in height (z-axis). Optionally, inflatable expandable prosthesis 202 is 1 mm to 10 mm in height. It should be understood that the deflated and/or inflated size of prosthesis 202 is adapted to fit for a patient's particular needs or to simulate the size and/or shape of the natural bursa, in an embodiment of the invention, and therefore, prosthesis 202 does not necessarily conform to the size ranges given above.

Inflatable expandable prosthesis 202 is manufactured by dip molding, in an exemplary embodiment of the invention. In some embodiments of the invention, inflatable expandable prosthesis 202 is a seamless balloon-like structure made from biocompatible and/or biodegradable synthetic materials such as, but not limited to, PCL, PGA, PHB, plastarch material, PEEK, zein, PLA, PDO and PLGA, or any combination and/or family members thereof. Additionally, optionally and/or alternatively, inflatable expandable prosthesis 202 is manufactured from natural, biocompatible and/or biodegradable materials such as collagen and/or methyl cellulose. In some exemplary embodiments of the invention, the inflatable prosthesis 202 is manufactured from at least one non-biodegradable material such polyethylene, polyurethane, silicon, and/or Kevlar®. In an embodiment of the invention, prosthesis 202 is comprised of a material which is approximately 100 microns in thickness, although, as with the other dimensions, the thickness dimension of the material is adapted depending on the intended use and/or the needs of the patient. In some exemplary embodiments of the invention, inflatable expandable prosthesis 202 is adapted to elute pharmaceuticals such as anti-inflammatory drugs and/or antibiotics and/or pro-angiogenesis factors to promote healing.

Inflatable expandable prosthesis 202 is releasably attached to prosthesis implantation and/or inflation device 200, in an exemplary embodiment of the invention. Prosthesis implantation and/or inflation device 200 is adapted to inflate and/or deflate prosthesis 202, allow prosthesis 202 to be positioned in vivo, and/or separate from prosthesis 202 after implantation, leaving prosthesis 202 at the implantation site, in an embodiment of the invention. In some exemplary embodiments of the invention, prosthesis implantation and/or inflation device 200 includes a tube or catheter type structure 204 which interfaces with prosthesis 202 in the proximity of a sealing mechanism 206 which is located at the end of tube 204 nearest prosthesis 202.

Figure 4A:
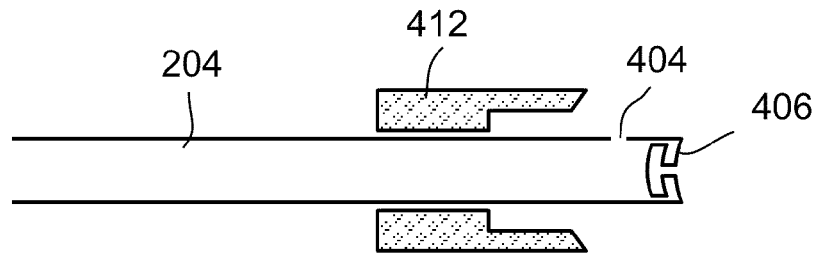
FIGS. 4A-C are cutaway side views showing the progression removably attaching a prosthesis implantation and/or inflation device and an expandable prosthesis, in accordance with an exemplary embodiment of the invention.
Figure 4B:
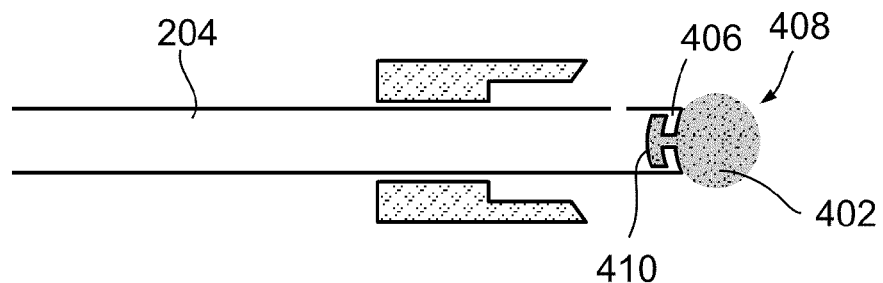

In an embodiment of the invention, sealing mechanism 206 includes a plug 402, shown in FIG. 4B inter alia, attached to the end of tube 204 nearest prosthesis 202. In an embodiment of the invention, plug 402 is constructed of the same material or materials as any of the prostheses described herein. Tube 204 is adapted to allow passage therethrough of the substance used to fill prosthesis 202, for example by placing at least one orifice 404 in tube 204. In some embodiments of the invention, air is used to inflate prosthesis 204. Additionally, alternatively and/or optionally, a biodegradable and/or biocompatible substance is used to inflate prosthesis 202. In some embodiments of the invention, a gel or liquid is used to inflate prosthesis 202. In an embodiment of the invention, tube 204 is provided with gripping protrusions 406 in order to increase the contact surface between tube 204 and plug 402 and therefore the force that may be applied to plug 402 when sealing prosthesis 202. In some embodiments of the invention, plug 402 is ovoid shaped, and/or has a shape such that plug's 402 loose end 408 is larger than the attached end 410 so that, as described in more detail below with respect to FIGS. 4A-C, 5 and 7, plug 402 seals inflatable expandable prosthesis 202 during implantation.

Figure 4C:
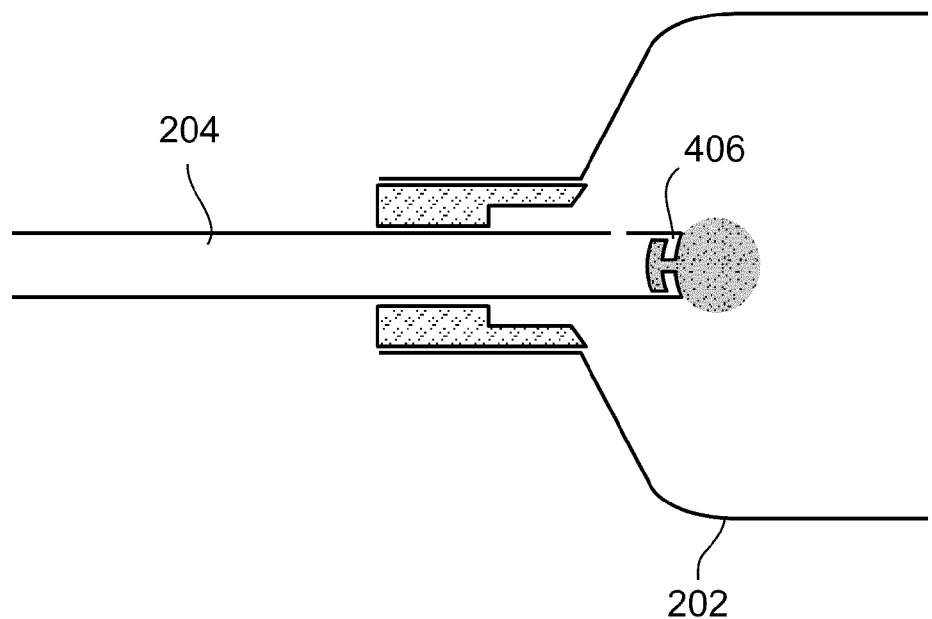

FIGS. 4A-C are cutaway side views showing the progression of removably attaching prosthesis implantation and/or inflation device 200 and prosthesis 202, in accordance with an exemplary embodiment of the invention. Referring to FIG. 4A, a rigid ring 412 is cast on tube 204 of prosthesis implantation and/or inflation device 200, in an embodiment of the invention. In an embodiment of the invention, rigid ring 412 fits snugly onto tube 204 such that air and/or other fluid injected into prosthesis 202 does not escape via the intersection of rigid ring 412 and tube 204, however tube 204 is slidable in relation to rigid ring 412. This slidability is useful, for example, when prosthesis implantation and/or inflation device 200 is separated from prosthesis 202 in accordance with an exemplary embodiment of the invention. In an exemplary embodiment of the invention, plug 402 is cast on tube 204 such that gripping protrusions 406 grasp at least a portion of attached end 410 of plug 402, shown in FIG. 4B. Optionally, dip molding, or any other method known in the art, is used for manufacturing plug. At least tube 204 and/or plug 402 and/or rigid ring 412 are made of biodegradable and/or biocompatible materials, in an embodiment of the invention.

Rigid ring 412 is cast on tube 204 before plug 402 is cast tube 204 because in an exemplary embodiment of the invention, plug 402 has a larger diameter than the inner diameter of rigid ring 412 thereby preventing plug 402 from passing through rigid ring 412. In an embodiment of the invention, inflatable expandable prosthesis 202 is placed around plug 402 and tube 204 such that tube 204 and plug 402 extend into a cavity proscribed by prosthesis 202. Prosthesis 202 is attached to an exterior surface of rigid ring 412 such that air and/or other fluid injected into prosthesis 202 does not escape via the intersection of prosthesis 202 and rigid ring 412, in an embodiment of the invention. Optionally, a thermal method is used to attach prosthesis 202 to rigid ring 412.

Figure 5:
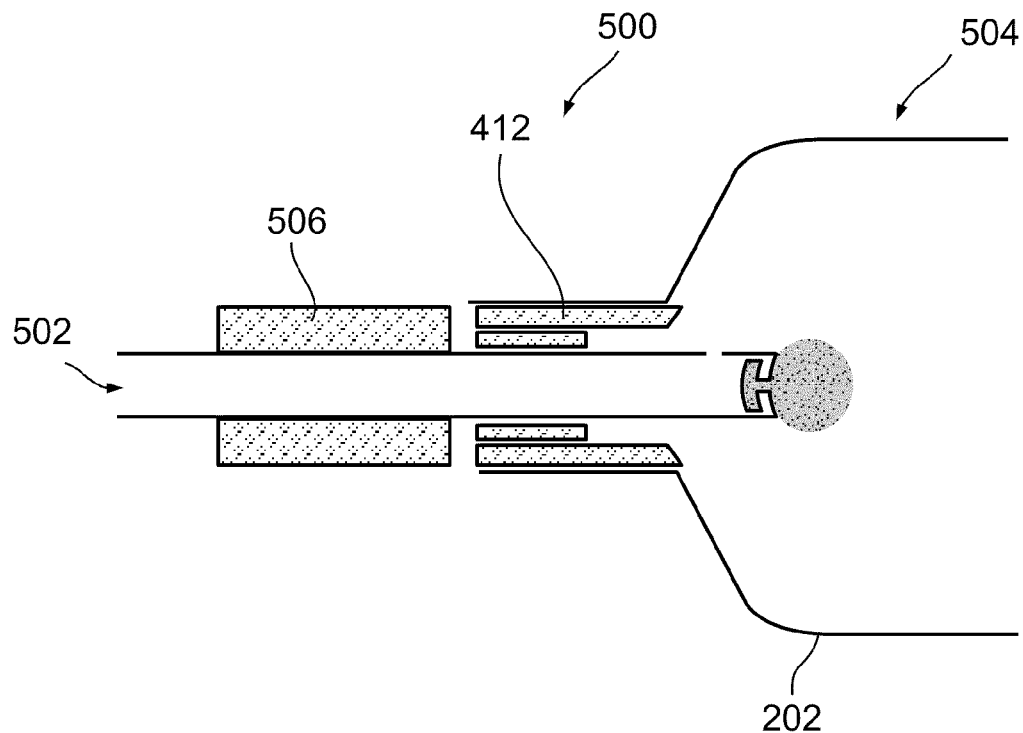
FIG. 5 is a cutaway side view of a portion of a prosthesis implantation and/or inflation device including a counter-pressure sheath and an expandable prosthesis, in accordance with an exemplary embodiment of the invention.

FIG. 5 shows an assembly 500 including a portion 502 of inflation device 200 and a portion 504 of expandable prosthesis 202 further comprising a counterforce ring 506, in accordance with an exemplary embodiment of the invention. In an embodiment of the invention, counterforce ring 506 is adapted to apply counterforce to rigid ring 412 during separation of prosthesis inflation device 200 from prosthesis 202, as described in more detail below with respect to FIG. 7. In some embodiments of the invention, counterforce ring 506 is constructed of a biocompatible material, for example stainless steel and/or plastic, that is approximately at least as hard as rigid ring 412.

Figure 6:
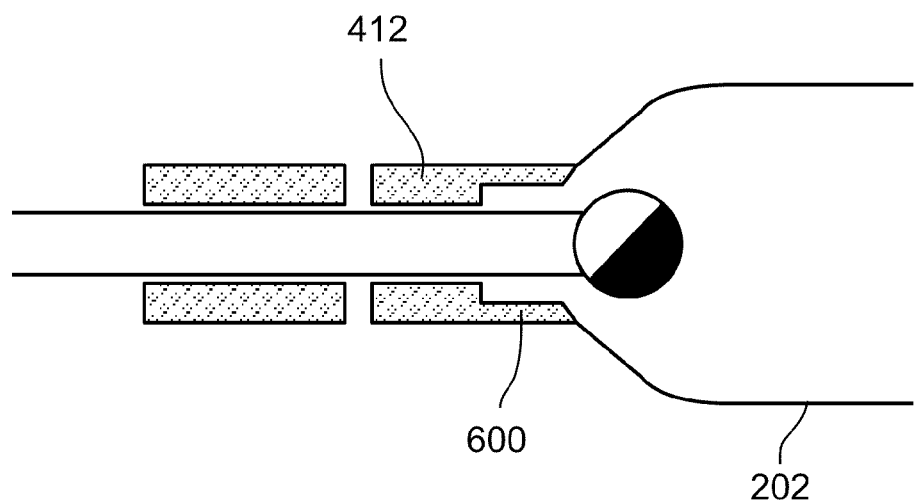
FIG. 6 is a cutaway side view of an alternative sealing mechanism, in accordance with an exemplary embodiment of the invention.

In some embodiments of the invention, at least one unidirectional valve 600, shown in FIG. 6, is used in addition to or alternatively to plug 402 and rigid ring 412 for sealing prosthesis 202 after at least partially inflating prosthesis 202 with prosthesis implantation and/or inflation device 200.

Figure 3:
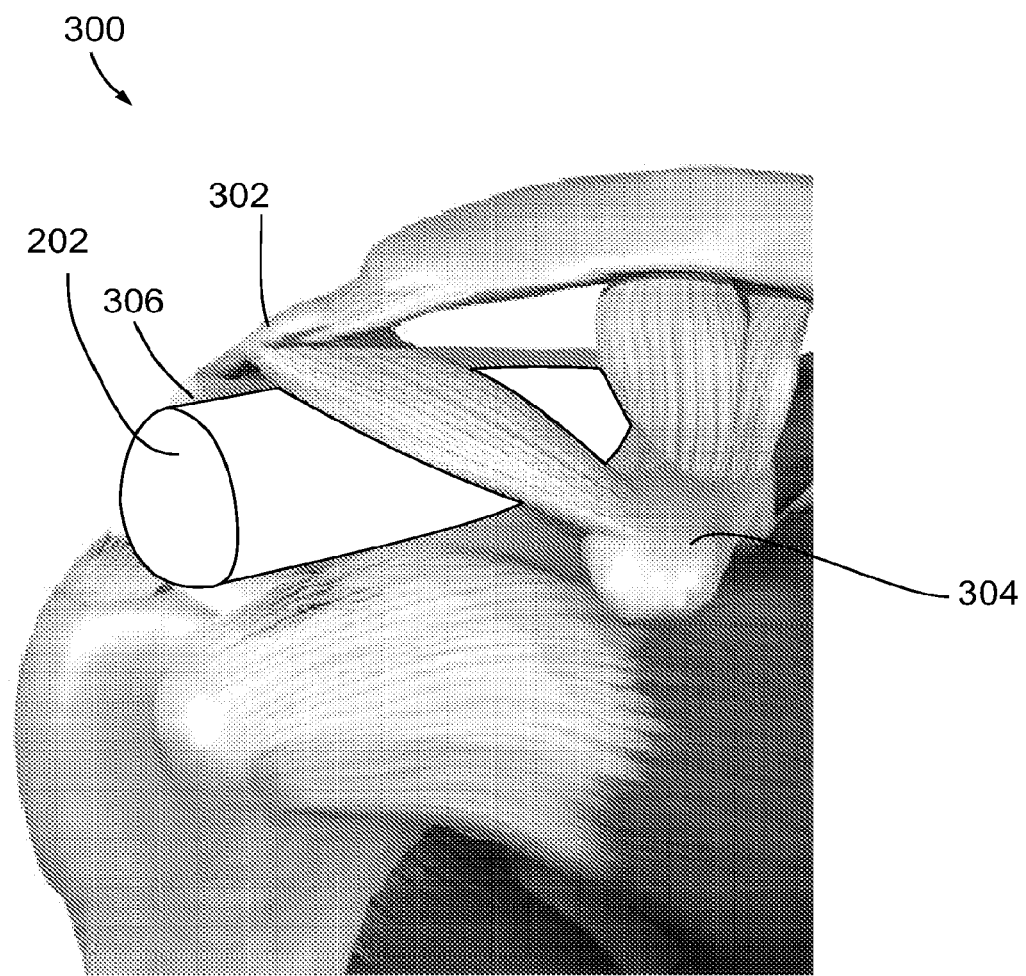
FIG. 3 is an anatomical view of a human shoulder with an expandable prosthesis in vivo, in accordance with an exemplary embodiment of the invention.

FIG. 3 shows an anatomical view of a human shoulder 300 with an expandable prosthesis 100, 202 in vivo, in accordance with an exemplary embodiment of the invention. Prosthesis 100, 202 is inserted between the acromion 302 and the coracoid process 304, in an embodiment of the invention. In some embodiments of the invention, prosthesis 100, 202 and any other prosthesis described herein, is inserted proximal to the bursa 306. Optionally, if there is no bursa 306 of any remarkable size, the prosthesis is inserted in lieu of bursa 306. In an embodiment of the invention, an implanted prosthesis, such as those described herein, is adapted to cover the humerus head during shoulder 300 motion, while remaining relatively fixed in relation to the acromion 302 and/or the coracoid process 304.

In some embodiments of the invention, an anchoring expandable prosthesis is adapted to prevent and/or reduce injury to the rotator cuff and/or to permit relatively unhindered or free shoulder movement. The anchoring expandable prosthesis comprises an expandable member and at least one anchoring device which is adapted to be attached to a part of the patient, for example the humerus head/tendons, acromion and/or coracoid process, thereby anchoring the prosthesis in place. In an embodiment of the invention, the anchoring expandable prosthesis comprises at least one anchoring device attached to an expandable portion adapted to operate similarly to prostheses 100, 202. The at least one anchoring device 308 is manufactured of biocompatible and/or biodegradable or non-biodegradable metals and/or alloys and/or composites, for example titanium, stainless steel or magnesium alloys. In an embodiment of the invention, the expandable portion is manufactured of biocompatible and/or biodegradable or non-biodegradable materials such as high density polyethylene or those described with respect to prostheses 100, 202. In an embodiment of the invention, the at least one anchoring device is attached to the expandable member using filaments and/or wires.

In some embodiments of the invention, prostheses described herein are adapted for anchoring, for example by contouring the outer surface such that surrounding tissues can be placed within the contours, thereby "anchoring" the device. In some embodiments of the invention, the contours are adapted to act as counterparts to anatomical features at the implantation site, whereby the features settle into the contours upon implantation, but still permit relatively unhindered movement of the treated area.

Prostheses 100, 202, and/or any of the other prostheses described herein, are adapted for use in places where there is sliding of soft tissues, such as tendons against other tissues, such as bones as: a) between the quadriceps and femur after operations on the knee, b) near the finger flexor and/or extensor to prevent adhesions, for treatment of ailments such as carpal tunnel syndrome or, c) between the skin and plantar fascia and calcaneus in case of calcaneal spur, in some exemplary embodiments of the invention. As described above, the prosthesis used for treatment of particular ailments is sized and/or shaped to simulate the natural bursa found at the location being treated, in an exemplary embodiment of the invention.

In an embodiment of the invention, an expandable prosthesis which is least slightly elastic, but not inflatable, is adapted to prevent and/or reduce injury to the rotator cuff and/or to permit relatively unhindered or free shoulder movement. In some embodiments of the invention, the elastic prosthesis is manufactured from polyethylene and/or silicon and/or in combination with metals, such as titanium. Optionally, the elastic prosthesis is contoured to serve as a counterpart to the surfaces with which it will come into contact. For example in the case of a rotator cuff, the elastic prosthesis may be contoured to fit at least the acromion.

In an embodiment of the invention, a prosthesis is provided which is substantially rigid. The rigid prosthesis is constructed of a biocompatible material, for example stainless steel and/or a hard plastic, in some embodiments of the invention. Optionally, the rigid prosthesis is also biodegradable. In some embodiments of the invention, the rigid prosthesis is adapted to act as a counterpart to at least one anatomical feature at the implantation site, whereby the feature mates with the rigid prosthesis upon implantation, but still permits relatively unhindered movement of the treated area. As an example, the rigid prosthesis is adapted to mate with both the humerus head and the acromion upon implantation, in an embodiment of the invention.

Figure 7:
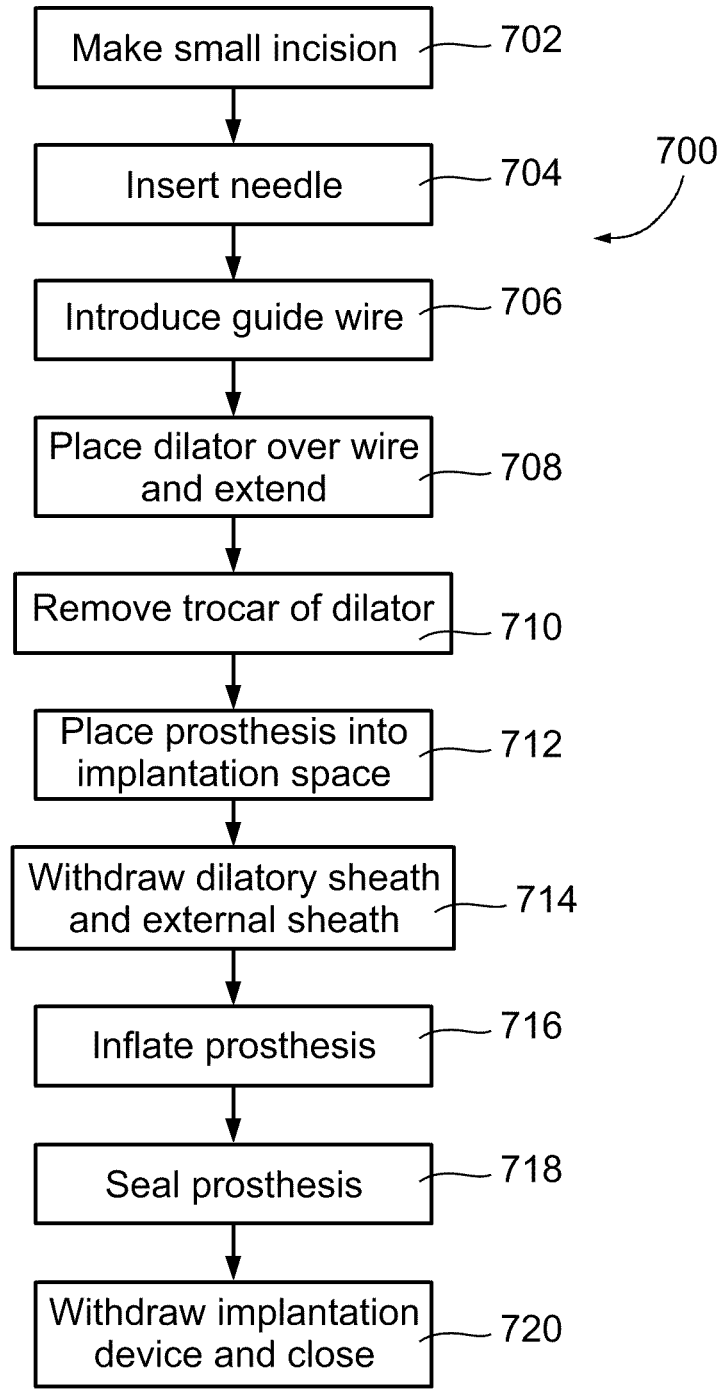
FIG. 7 is a flowchart demonstrating a method of implanting an expandable prosthesis, in some exemplary embodiments of the invention.

Referring to FIG. 7, a method 700 of implanting an expandable prosthesis 100, 202, or any other prosthesis described herein is described, in some exemplary embodiments of the invention. In an embodiment of the invention, implantation method 700 is adapted for implantation of prostheses 100, 202, or any other prosthesis described herein, into the shoulder of a patient to prevent and/or reduce injury to the rotator cuff and/or to permit relatively unhindered or free shoulder movement. In an embodiment of the invention, prostheses 100, 202, or any other prosthesis described herein, are introduced percutaneously or by making (702) a small incision, optionally performed by posterior, lateral or anterior approaches using, for example, palpation, arthroscopy, ultrasound ("US"), computed tomography ("CT"), magnetic resonance imaging ("MRI"), fluoroscopy, transmission scan ("TX"), or any combination thereof. In an embodiment of the invention, a needle is inserted (704) into the space between the rotator cuff tendons and the acromion 302 and coracoid process 304. A guide wire is introduced (706) via the needle into the space between the rotator cuff tendons and the acromion 302 and coracoid process 304, in an exemplary embodiment of the invention. In some embodiments of the invention, a dilator is placed (708) over the guide wire and extended into the space. Subsequently, a trocar of the dilator is removed (710), leaving a dilator sheath in place.

Figure 8:
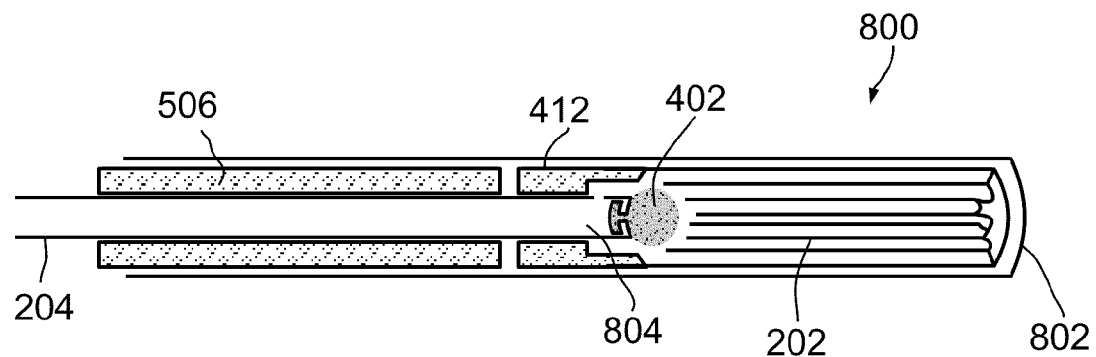
FIG. 8 is a cutaway side view of an expandable prosthesis packed prior to use, in accordance with an exemplary embodiment of the invention.

In an embodiment of the invention, inflatable expandable prosthesis 202 is placed (712) into the space using the dilator sheath and/or the prosthesis inflation device 200 for guidance and/or movement impetus. Once prosthesis 202 is approximately in the proper position, the dilator sheath and an external sheath 802 of prosthesis inflation device 200, shown and described in more detail with respect to FIG. 8, are withdrawn (714) to allow for inflation (716) of prosthesis 202. Inflation (716) using prosthesis inflation device 200 is described in more detail below. Inflation (716) of prosthesis 202 is achieved, in some embodiments of the invention, during arthroscopy. In some embodiments of the invention, for example if prosthesis 202 is implanted during open surgery or arthroscopy, proper deployment of prosthesis 202 is ascertained by visual inspection of prosthesis 202. In an embodiment using arthroscopy, prosthesis may be introduced through an arthroscopy port. In some embodiments of the invention, inflation (716) is achieved using palpation and US guidance to ascertain proper deployment of prosthesis 202. In some embodiments of the invention, inflation (716) is achieved using fluoroscopy to ascertain proper deployment of prosthesis 202. Proper deployment of prostheses, in some embodiments of the invention, means no interposition of tendons and/or other soft tissue between the implanted prosthesis and acromion 302 or coracoid process 304 and/or that during movement of the humerus, the prosthesis remains below acromion 302.

Inflation (716) of prosthesis 202 is performed using prosthesis inflation device 200, in an embodiment of the invention. It should be understood that only a portion of prosthesis inflation device 200 is shown in FIG. 2, and that exemplary variations are shown in more detail with respect to FIGS. 16-17. Referring to FIG. 8, an expandable prosthesis 202 is shown packed for implantation and prior to deployment, in accordance with an exemplary embodiment of the invention. Components of the assembly 800 are enclosed in an external sheath 802 which surrounds at least prosthesis 202, in an exemplary embodiment of the invention. External sheath 802 is adapted to maintain prosthesis 202 in a collapsed condition during placing (712) in order to ease insertion of prosthesis 202 into the implantation space or site through the dilator sheath, in an embodiment of the invention. As described above, once prosthesis 202 is in the implantation space, external sheath 802 is removed, enabling prosthesis 202 to be inflated without hindrance apart from the body parts against which prosthesis 202 is pressing.

In an embodiment of the invention, inflation (716) of prosthesis 202 is performed using a physiologic fluid such as saline, Hartman or Ringer solutions and/or any other biocompatible and/or biodegradable fluid. In some embodiments of the invention, inflation (716) is performed using a biocompatible and/or biodegradable gel. In an embodiment of the invention, inflation (716) of prosthesis 202 is performed using a gas, for example air and/or carbon dioxide. In some embodiments of the invention, the inflating gel and/or fluid contains pharmaceutical agents, for example anti-inflammatory drugs and/or antibiotics and/or pro-angiogenesis factors to promote healing, which are eluted into the patient's body. In some embodiments of the invention, prosthesis 202 is inflated to the maximum volume possible without reducing the shoulder's range of movement. In an embodiment of the invention, prosthesis 202 is filled to less than its maximum volume in order to permit shifting of the contents of prosthesis 202 during movement. Optionally, prosthesis 202 is filled to 60%-70% of its maximum volume (for example, an expandable member with a 14 cc volume is filled with 9 cc of filler). It should be noted that other prosthesis embodiments described herein are deployed in a similar fashion, in some embodiments of the invention.

Sealing (718) of prosthesis 202, once inflated to the desired level, is performed by pulling tube 204 towards rigid ring 412 as they slide in relation to one another plug 402 becomes lodged in a lumen 804 of rigid ring 412 and continued pulling brings rigid ring 412 into contact with counterforce ring 506, in an embodiment of the invention. In an embodiment of the invention, tube 204 passes through lumen 804 with lumen 804 providing fluid communication between prosthesis implantation and/or inflation device 200 and an inner space defined by the dimensions of prosthesis 202. In an embodiment of the invention, an attending medical professional performing the implantation procedure holds counterforce ring 506 substantially steady while pulling on tube 204 away from the patient.

Optionally, prosthesis inflation device 200 is adapted to perform the steadying of counterforce ring 506 and/or retraction of tube 204 automatically. In some embodiments of the invention, a mechanism is provided to prosthesis inflation device 200 which translates rotational movement to a retracting force on tube 204. Optionally, rotation movement is applied manually.

Continued pulling ("retraction" away from patient) of tube 204 causes a portion of plug 402 to break off, the portion of plug 402 lodging itself in lumen 804 of rigid ring 412 thereby sealing prosthesis 202. In some embodiments of the invention, the portion of plug 402 becomes partially deformed as it lodges in lumen 804. Prosthesis inflation device 200, now being separated from prosthesis 202 as a result of sealing (718) is withdrawn (720) from the patient and patient is closed, in an exemplary embodiment of the invention. It should be understood that in some embodiments of the invention, a sponge-like expandable prosthesis device is used and therefore, inflation (716) and inflation related actions may not be carried out, for example prosthesis 100 expands rather than inflates.

In an exemplary embodiment of the invention, the implanted prosthesis is secured, using methods known in the art, to soft tissue and/or bone to prevent the prosthesis from being easily displaced by shoulder movement. In some embodiments of the invention, sutures, clips and/or anchors are used to secure the prosthesis in place. Optionally, an anchoring expandable prosthesis is used. In an embodiment of the invention, simulating a naturally occurring bursa using a prosthesis is an action taken with respect to method 700. Optionally, simulating is related to inflation (716) in that the prosthesis is inflated to resemble the appropriate size and/or shape and/or characteristics (malleability, compressibility, etc.) of the naturally occurring bursa. In an embodiment of the invention, placing the prosthesis at the implantation site and simulating a naturally occurring bursa does not significantly reduce movement of the soft tissues being protected in relation to the other tissues at the implantation site.

In an exemplary embodiment of the invention, prosthesis 100 is implanted by placing prosthesis 100 into a cannula, such as those described elsewhere herein, and advancing it to the implantation site using a plunger.

In an exemplary embodiment of the invention, prosthesis 100 or the elastic prosthesis, described above, is implanted by inserting the device directly through a small incision, without a cannula, near the implantation site.

It should be noted that the method shown and described with respect to FIG. 7 is by way of example only, and that similar methods could be used for implantation of any bursa simulating prosthesis adapted for reducing injuries between soft tissues and other tissues of the body.

Figure 9:
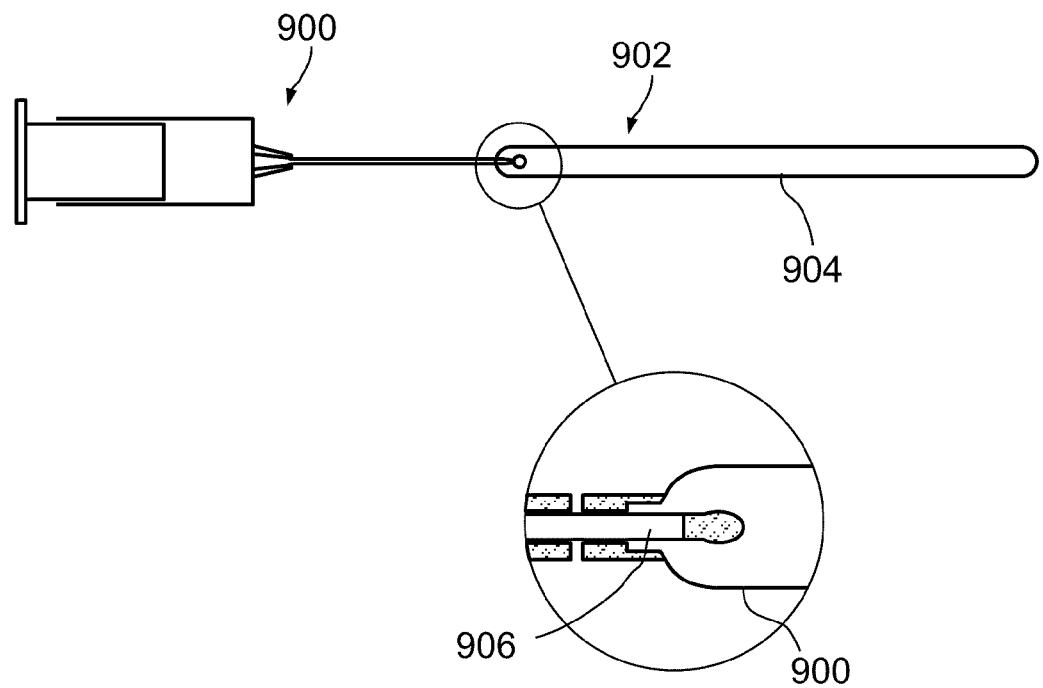
FIG. 9 is a cutaway side view of a portion of a prosthesis implantation and/or inflation device and an expandable prosthesis for alignment of bone fragments, in accordance with an exemplary embodiment of the invention.

Referring to FIG. 9, a cutaway side view of a portion of a prosthesis implantation and/or inflation device 900 and an expandable prosthesis 902 for alignment of bone fragments in the case of fractures of tubular bones is shown, in accordance with an exemplary embodiment of the invention. Prosthesis 902 is adapted to fit in the medullar cavity of the bone in which it is intended to be used and is optionally biodegradable and/or biocompatible. In an embodiment of the invention, prosthesis 902 is intended to be used in non-weight bearing bones, for example, the humerus, radius, and ulna. Prosthesis 902 comprises an inflatable tubular member 904 which is generally shaped to fit within a medullar cavity of the bones to be aligned. Optionally, inflatable tubular member 904 is tubular or vasiform. Optionally, inflatable tubular member 904 is slightly curved. In an embodiment of the invention, inflatable tubular member 904 has an approximate outer diameter ranging between 2 to 15 mm and having an approximate length ranging between 5 to 50 cm. Optionally, the outer diameter ranges between 4 to 10 mm. Optionally, the length ranges between 10 and 30 cm. In an embodiment of the invention, prosthesis 902 is sized and/or shaped to fit into the medullar cavities of the bone fragments which are intended to be aligned.

Prosthesis 902 is releasably attached to prosthesis implantation and/or inflation device 900 and/or inflated in a similar fashion as described with respect to prosthesis 202 and implantation and/or inflation device 200, in an embodiment of the invention.

At least part of prosthesis 902 (e.g. tubular member 904) is manufactured, in an embodiment of the invention, by dip molding. Optionally, inflatable tubular member 904 is a seamless balloon made from biocompatible and/or biodegradable synthetic materials such as, but not limited to, PLA, PLGA, PCL, PDO, or any combination and/or families thereof. In an embodiment of the invention, inflatable tubular member 904 is provided with an outer wall thickness adapted to accommodate at least a minimum level of rigidity necessary to maintain the aligned bone fragments during normal activity. For example, forearm bones are normally subjected to forces ranging from a few hundred grams to several kilograms during normal activity. As another example, metacarpal bones are normally subjected to tens of grams to a few hundred grams of force. It should be noted that these ranges are provided as examples only and that depending on patient and/or the bone fragments being aligned, the wall thickness of inflatable tubular member will be adapted to maintain alignment of the bone fragments in spite of the anticipated stress on prosthesis 902 during normal activity and/or rehabilitation of the patient.

In an exemplary embodiment of the invention, inflation of prosthesis 902 is performed using a physiologic fluid such as saline, Hartman or Ringer solutions and/or any other biocompatible and/or biodegradable fluid. In some embodiments of the invention, inflation is performed using a biocompatible and/or biodegradable gel. In an embodiment of the invention, inflation of prosthesis 902 is performed using a gas, for example air and/or carbon dioxide. In an embodiment of the invention, prosthesis 902 is filled with a cement that hardens and/or seals the open end 906 of prosthesis 902. In some embodiments of the invention, the cement is used provide alignment for the fractured bone segments.

In an exemplary embodiment of the invention, prosthesis 902 is adapted to elute at least one pharmaceutical agent, for example anti-inflammatory drugs and/or antibiotics and/or bone deposition promoting factors and/or pro-angiogenesis factors to promote healing of the fracture.

In some embodiments of the invention, prosthesis 902 (and/or other prostheses described herein) is used with a calibration kit which determines the size of the medullar cavity and/or the proper size inflatable tubular member 904 to use with the medullar cavity. Optionally, the calibration kit is integrated with prosthesis 902. Optionally, the calibration kit is integrated with prosthesis implantation and/or inflation device 900. In an embodiment of the invention, a calibration expandable member is first deployed into the medullar cavity to measure the cavity shape and/or size and then upon deployment of prosthesis 902, its shape and/or size is adapted to match the needs of the measured medullar cavity. Optionally, various sizes of dilators are used in conjunction with the calibration expandable member to assist with determining size.

Figure 10:
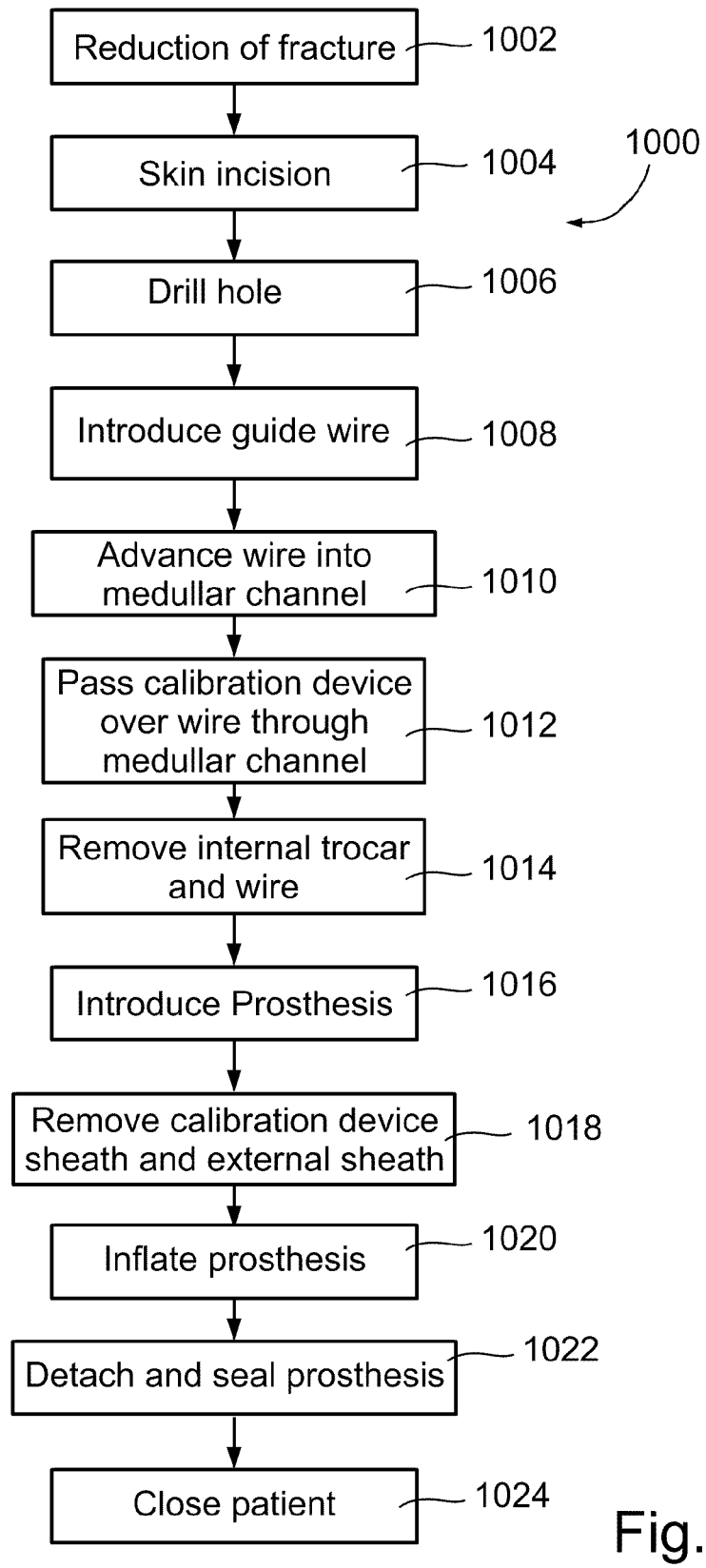
FIG. 10 is a flowchart showing a method of aligning two or more segments of bone, in accordance with an exemplary embodiment of the invention.

FIG. 10 is a flowchart 1000 showing a method of aligning two or more segments of bone, in accordance with an exemplary embodiment of the invention. Reduction (1002) of the fracture is performed, in an exemplary embodiment of the invention, by closed reduction. The closed reduction maneuvers are performed under fluoroscopic and/or TX guidance, in some embodiments of the invention. A skin incision is performed (1004) over a first segment of bone. In an embodiment of the invention, a hole is drilled (1006) through the compact bone of one of the bone segments near the epiphyseal plate into the medullar channel and a guide wire is introduced (1008) through this medullar channel and advanced (1010) into the medullar channel of the other segment of bone passing through the fracture site. When more than two fragments of bone exist, in an embodiment of the invention, the wire passes through the medullar channels of all segments.

A calibration device comprising a sheath and an internal trocar is passed (1012) over the wire through the medullar channels of the bone segments, in an embodiment of the invention. The internal trocar and the wire are removed (1014) leaving inside only the external sheath of the calibration device within the medullar channel of the bone segments, in an exemplary embodiment of the invention. Prosthesis 902 is introduced (1016) into this sheath, in an embodiment of the invention. The calibration device sheath and the external sheath of prosthesis 902 (similar in form and function to external sheath 802) are removed (1018) in an embodiment of the invention and the unexpanded prosthesis 902 remains in the medullar channels of the segments of bone.

Figure 11:
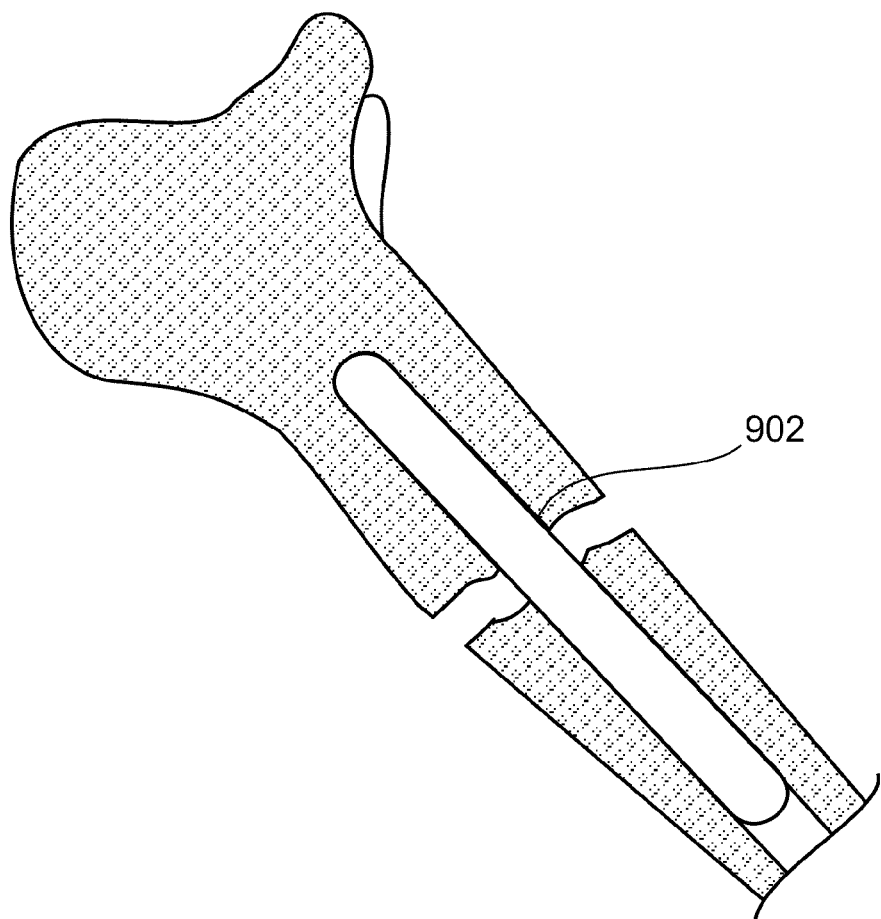
FIG. 11 is a cutaway side view of an expandable prosthesis for aligning bone fragments in vivo, in accordance with an exemplary embodiment of the invention.

In an embodiment of the invention, prosthesis 902 is inflated (1020) as described above with a biocompatible and/or biodegradable filler and the prosthesis 902 is detached (1022) sealing prosthesis 902 under pressure. The sealing is performed using any of the previously described methods or by any method known to those skilled in the art. In an embodiment of the invention, prosthesis 902 remains within the reduced bone segments keeping them in alignment, as shown in FIG. 11. The skin incision is closed (1024). In some embodiments of the invention, healing of the bone fragments is accelerated by eluting pharmaceutical agents from prosthesis 902.

In an embodiment of the invention, alignment of the bone segments is maintained by the rigidity of prosthesis 902. In an embodiment of the invention, the rigidity of prosthesis 902 at least partly depends on the internal pressure of prosthesis 902, the internal pressure being at least partly determined by the filler used and/or the percentage of prosthesis 902 that is filled by the filler. Optionally, an external cast is placed on the area proximal to the fracture.

Figure 12:
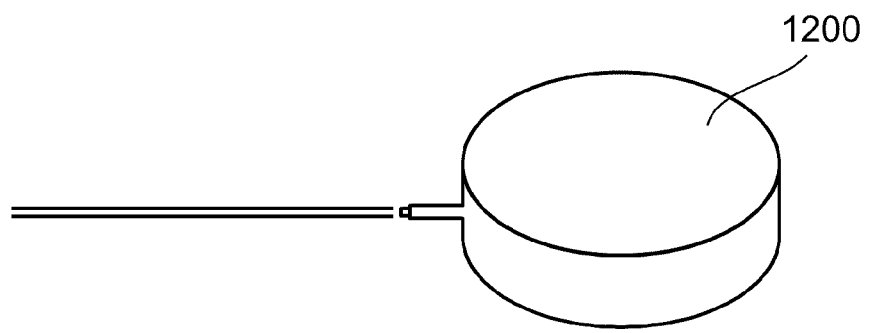
FIG. 12 is a perspective view of a device for treating inflammation and/or infection, in accordance with an exemplary embodiment of the invention.

FIG. 12 is a perspective view of a device 1200 for treating inflammation and/or infection, in accordance with an exemplary embodiment of the invention. In an embodiment of the invention, device 1200 is a sponge-like structure. In some embodiments of the invention, device 1200 is an inflatable structure. Device 1200 is adapted to be placed at a site in the body for treating inflammation and/or infection, in an embodiment of the invention, in an embodiment of the invention.

In an exemplary embodiment of the invention, a sponge-like device 1200 is manufactured of biocompatible and/or biodegradable synthetic materials such as, but not limited to, PLA, PLGA, PCL, PDO, or any combination thereof. Alternatively and/or additionally and/or optionally, it may be manufactured from biologically derived biodegradable materials such as collagen. Expandable sponge-like device 1200 optionally contains within its cavities at least one biocompatible and/or biodegradable gelling material, such as methyl cellulose, agarose, poly(ethylene-glycol) ("PEG") gel and/or PLA gel, that expands when it comes into contact with at least one bodily fluid, for example by absorbing water. In an embodiment of the invention, such absorption is partly responsible for an expansion of sponge-like device 1200 into its intended deployed position.

As described above, in some exemplary embodiments of the invention, device 1200 comprises an inflatable structure. In an embodiment of the invention, inflatable device 1200 is constructed of at least one biocompatible and/or biodegradable material, such as those described herein. In some embodiments of the invention, inflatable device 1200 is spherical or cylindrical, having a diameter of 0.5 cm to 5 cm for a sphere or in the long direction (x-axis) and 0.5 cm to 4 cm in the short direction (y-axis) and a height (z-axis) of 0.5 mm to 20 mm. In some embodiments of the invention, device 1200 is adapted to be inserted deflated into a patient's body through a cannula. Optionally, the cannula is a 5 mm-7 mm cannula. Optionally, device 1200 dimensions are adapted for a particular intended use.

In some exemplary embodiments, device 1200 is inflated and/or implanted as described herein with respect to prostheses 100, 202, 902. Device 1200 optionally contains pharmaceutical agents, for example anti-inflammatory drugs and/or antibiotics and/or pro-angiogenesis factors to promote healing, which are eluted into the body. In some embodiments of the invention, device 1200 is adapted to elute pharmaceutical agents according to a predefined schedule. Adaptation of device 1200 includes construction of device 1200 using materials or combinations of materials which degrade at a predetermined rate, thereby releasing pharmaceutical agents contained therein at a predetermined rate. In an exemplary embodiment of the invention, more than one device 1200 is used for treating inflammation and/or infection. Optionally, each device is adapted to elute pharmaceutical agents in view of an overall plan incorporating a plurality of devices.

In another exemplary embodiment of the invention, an expandable device, such as those described herein, is adapted to be used near an articulation to reinforce the articular capsule. In an embodiment of the invention, the expandable device is introduced in anterior fashion to the shoulder articulation between the articular capsule and the deltoid and pectoralis muscle, in order to prevent recurrent dislocation of the shoulder. In another embodiment, the expandable device is introduced in front of the hip joint capsule to prevent anterior dislocation of the hip, especially in cases of congenital dysplasia of hip. In an exemplary embodiment of the invention, the expandable device consists of in inflatable member made of biocompatible and/or biodegradable material. In some embodiments of the invention, the expandable device has a diameter of 1 cm to 7 cm in the long direction (x-axis) and 1 cm to 5 cm in the short direction (y-axis) with a height (z-axis) of 0.5 mm to 25 mm. Optionally, the device has a height of 3 mm to 15 mm.

Figure 13:
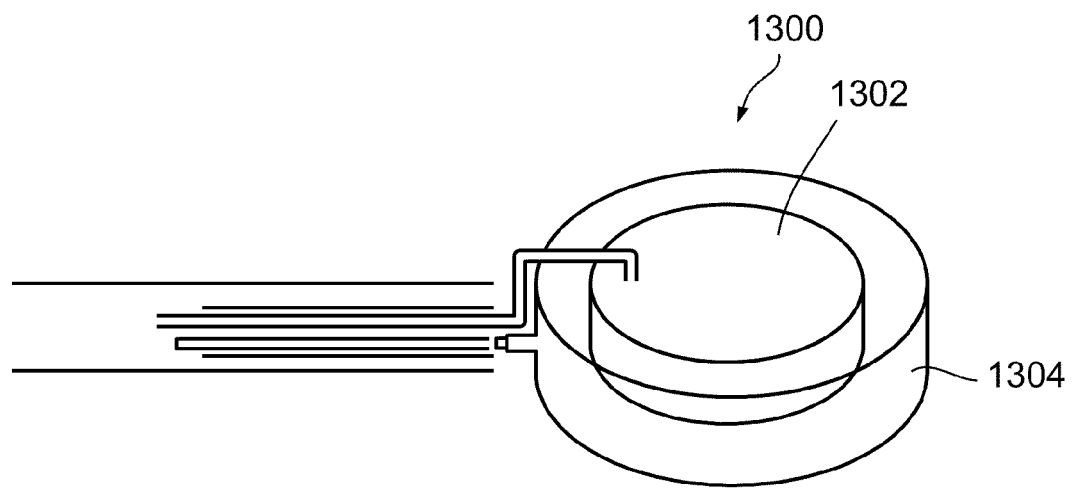
FIG. 13 is a perspective view of a device for treating depressed fractures, in accordance with an exemplary embodiment of the invention.

FIG. 13 shows a perspective view of a device 1300 for treating depressed fractures, for example osteoporotic fractures of the vertebra, in accordance with an exemplary embodiment of the invention. In some exemplary embodiments of the invention, device 1300 comprises at least two separately expandable sections, an inner section 1302 and an outer section 1304. In an embodiment of the invention, at least one expandable section is inflatable. In some embodiments of the invention, inner section 1302 when inflated takes a cylindrical shape measuring approximately 2 to 7 cm in diameter and 2 to 5 cm in height. Optionally, inner section 1302 is larger or smaller depending on the intended use of device 1300 and/or the particular needs of the patient. Inner section 1302 is manufactured from materials such as polyurethane, ultra high molecular weight polyethylene ("Spectra®") and/ or Kevlar® and/or any reinforced material that can withstand expected pressures on device 1300 as a result of the intended use, in an embodiment of the invention. In some embodiments of the invention, inner section 1302 is manufactured from a biocompatible and/or biodegradable substance such as PCL, PGA, PHB, plastarch material, PEEK, zein, PLA, PDO and PLGA, collagen, methyl cellulose, or any combination and/or family members thereof.

Expandable outer section 1304 at least partially surrounds inner section 1302, in an exemplary embodiment of the invention. In some embodiments of the invention, external section is a sponge-like structure, for example like other sponge-like structures described herein. Optionally, outer section 1304 is an inflatable structure, for example like other inflatable structures described herein. In some exemplary embodiments of the invention, outer section 1304 resembles a hollow cylinder, wheel and/or torus. In some embodiments of the invention, outer section 1304 is made of a biocompatible and/or biodegradable material, such as those described herein and known to those in the art.

In an embodiment of the invention, inner section 1302 and outer section 1304 are operatively connected to separate inflation devices. Optionally, only one inflation device is needed, for example if outer section 1304 or internal section 1302 is a sponge-like structure. In some exemplary embodiments of the invention, components of device 1300 are removably attached to at least one inflation device such as described elsewhere herein.

Figure 14:
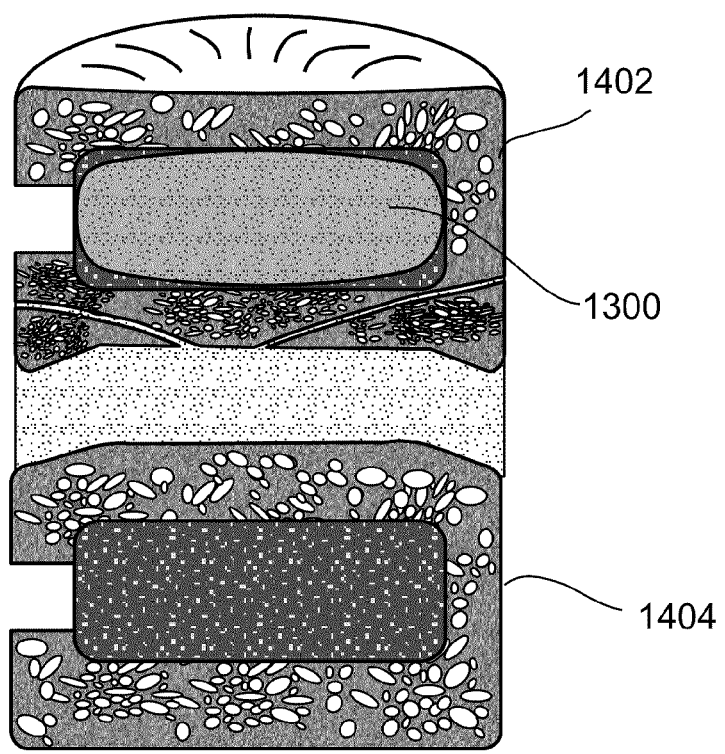
FIG. 14 is a perspective view, with a cutaway side view of two vertebrae, of a device for treating depressed fractures of vertebrae, in accordance with an embodiment of the invention.

FIG. 14 is a perspective view, with a cutaway side view of two vertebrae 1402, 1404, of a device 1300 for treating depressed fractures of a vertebra in vivo, in accordance with an embodiment of the invention. In some embodiments of the invention, device 1300 is adapted to treat osteoporotic fractures of vertebrae. As described below, device 1300 is used to deploy a filler, for example cement, to act as a force for restoring the natural shape of the fractured vertebra, thereby relieving pain and restoring at least a modicum of function to the patient.

Figure 15:
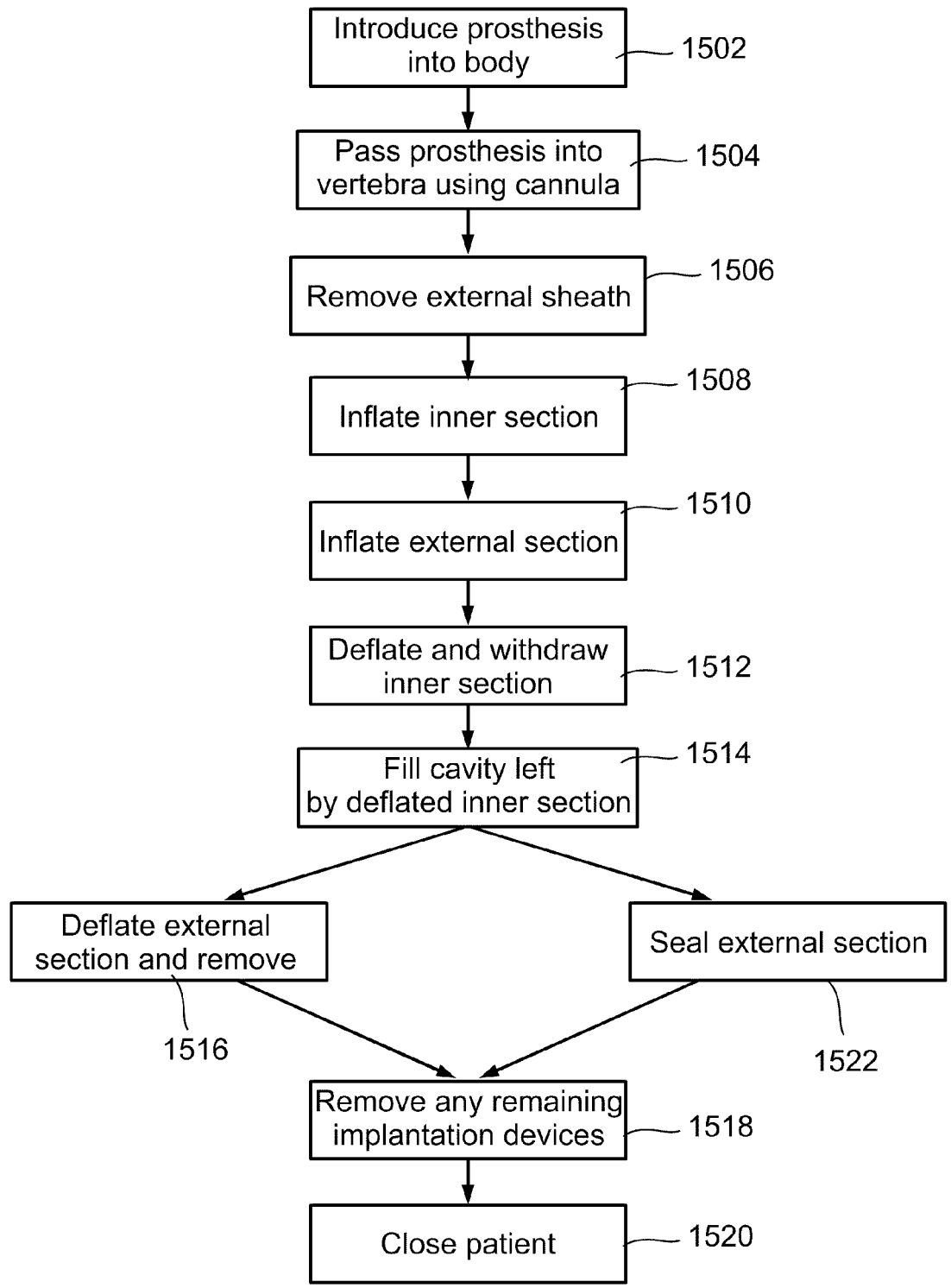
FIG. 15 is a flowchart showing a method of treating depressed fractures, in accordance with an exemplary embodiment of the invention.

FIG. 15 is a flowchart 1500 showing a method of treating depressed fractures, in accordance with an exemplary embodiment of the invention. In an exemplary embodiment of the invention, device 1300 is introduced (1502) to an implantation area using fluoroscopic, CT, MRI and/or TX guidance. Using a cannula, device 1300 is passed (1504) into vertebra 1402 whereby the depressed fracture is concave in relation to the implantation area, in an embodiment of the invention. An external sheath (similar in form and function of external sheath 802) of device 1300 is removed (1506) and inner section 1302 is inflated (1508) with a biocompatible filler until the bone regains its intended shape, in an embodiment of the invention. Outer section 1304 is then inflated (1510) and internal section 1302 is deflated and optionally withdrawn (1512) from the implantation area, in an embodiment of the invention. In an embodiment of the invention, the bone whose fracture has been reduced is reinforced by filling (1514) the cavity left in external section 1304 by optional withdrawal (1512) and/or deflation of inner section 1302 with at least one biocompatible and/or biodegradable filler, for example a cement. In an exemplary embodiment of the invention, outer section 1304 is deflated (1516) and optionally removed, any implantation devices remaining in use are removed (1518) and the patient is closed (1520). Alternatively, outer section 1304 is sealed (1522) in an inflated state, for example as described herein with respect to other embodiments, and remains in place permanently or until it biodegrades.

Figure 16:
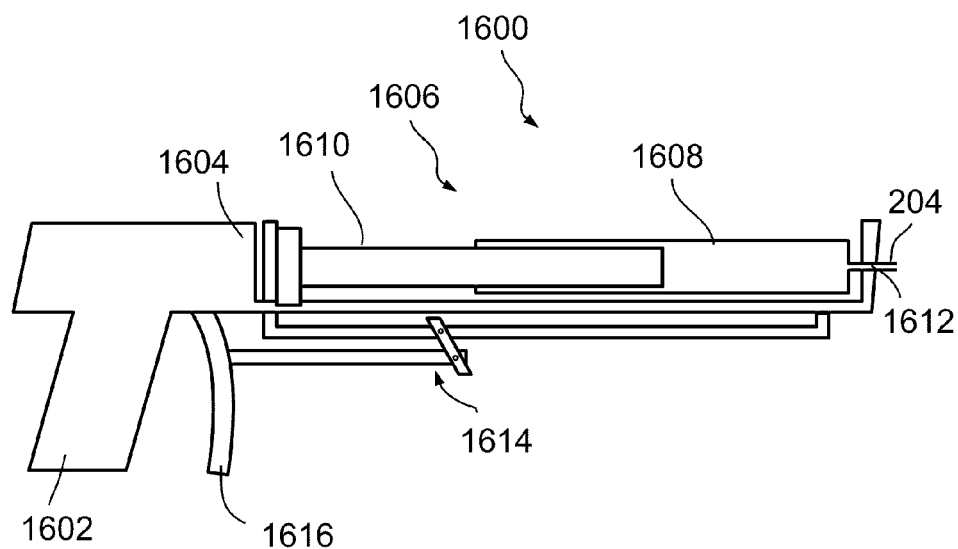
FIG. 16 is a cutaway side view of a prosthetic inflation device, in accordance with an exemplary embodiment of the invention; and, FIG. 17 is a cutaway side view of an alternate prosthetic inflation device, in accordance with an exemplary embodiment of the invention.

Referring to FIG. 16, a cutaway side view of a prosthetic inflation and/or implantation device 1600 is shown, in accordance with an exemplary embodiment of the invention. Prosthesis inflation and/or implantation device 1600 includes a grip 1602 adapted to be grasped in one hand by a medical professional performing the implantation procedure, in an embodiment of the invention. In some embodiments of the invention, device 1600 includes a housing 1604 adapted to mount therein a device inflation mechanism, for example a syringe 1606 comprising at least a canister 1608 and a plunger 1610, plunger 1610 adapted to travel within canister 1608 and expel filler out of canister 1608 via an outlet 1612 and into tube 204, described above. In an embodiment of the invention, syringe 1606 is adapted to hold and/or inject 5-20 cc of filler. It should be noted however, that syringe 1606 is adapted to hold and/or or inject more or less filler depending on the intended application of syringe 1606 and/or needs of the patient. In some embodiments of the invention, device 1600 includes a compression assembly 1614 adapted to apply force for at least for advancement of plunger 1610 in canister 1608 upon activation of a trigger 1616. Additionally and/or optionally, compression assembly 1614 is adapted to apply force for retraction of plunger 1610. In some embodiments of the invention, device 1600 is used to direct a prosthesis into an implantation site, as the prosthesis is removably connected to device 1600 via tube 204.

Figure 17:
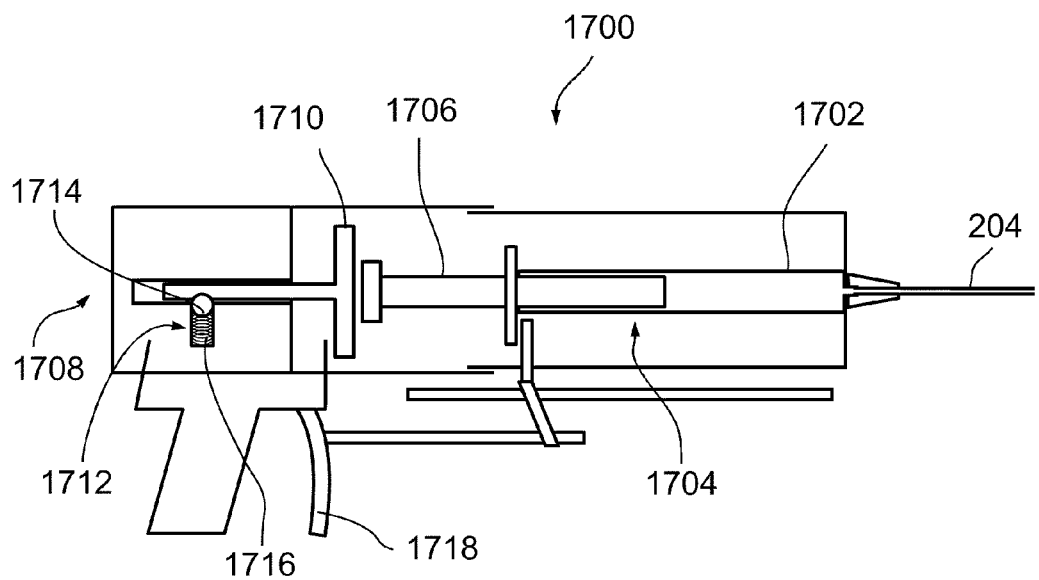

Referring to FIG. 17, a cutaway side view of an alternate prosthetic inflation and/or implantation device 1700 is shown, in accordance with an exemplary embodiment of the invention. In contrast to device 1600, which advances and/or retracts plunger 1610, device 1700 is adapted to advance and/or retract a canister 1702 portion of a syringe 1704 with a plunger 1706 portion remaining relatively fixed in relation to device 1700. Plunger 1706 portion is provided with counterforce, as canister 1702 portion is moved towards a proximal end 1708 of device 1700, by a backstop 1710, in an embodiment of the invention. Backstop 1710, in some exemplary embodiments of the invention, is fixed to device 1700. In an embodiment of the invention, the placement of the backstop is according to a predetermined level of desired inflation of the prosthesis.

In an embodiment of the invention, device 1700 is provided with a safety 1712 at least to prevent over-inflation of a prosthesis attached thereto. Safety 1712 in some embodiments of the invention, is comprised of a ball 1714 and a spring 1716 whereby ball 1714 and backstop 1710 are adapted to be counterparts such that ball 1714 releasably fits into a groove on backstop 1710 shaped to receive ball 1714. In an embodiment of the invention, once canister 1702 is advanced maximally by depressing a trigger 1718, further force on trigger 1718 will cause safety 1712 to disengage backstop 1710 as a result of ball 1714 popping out of the groove on backstop 1710 as backstop 1710 moves towards proximal end 1708 under the effect of further force. It should be noted that once safety 1712 has disengaged backstop 1710 and therefore, syringe 1704 is no longer being provided with a counterforce, continued depressing of trigger 1718 results in at least a partial retraction of tube 204 and appurtenant parts. In an embodiment of the invention, device 1700 is adapted to be used by one hand of an attending medical professional.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

The invention claimed is:

1. A method for implanting a prosthesis in a human shoulder, the method comprising:
providing an inflatable prosthesis;
placing the prosthesis proximal to, or in lieu of, a naturally occurring bursa between humerus and scapula in the shoulder;
inflating the prosthesis to a size or a shape of a naturally occurring bursa and to resemble characteristics of at least one of malleability and compressibility of the naturally occurring bursa; and
sealing the prosthesis;
wherein the sealed implanted prosthesis is configured to: (1) reduce rubbing of soft tissues against other tissues of at least one of a humerus, the acromion or the coracoid process of the shoulder while permitting at least some movement of the soft tissues relative to the humerus, the acromion or the coracoid process, and (2) permit relatively unhindered or free shoulder movement, and
wherein the prosthesis is deployed such that there is no interposition of the soft tissues between the implanted prosthesis and the acromion or the coracoid process, and the implanted prosthesis remains below the acromion during movement of the humerus.

2. A method according to claim 1, further comprising eluting at least one pharmaceutical agent from the prosthesis.

3. A method according to claim 1, wherein the soft tissues are tendons of a rotator cuff.

4. A method according to claim 1, wherein the prosthesis is a seamless balloon-like structure made from a biocompatible and/or a biodegradable synthetic material.

5. A method according to claim 1, further comprising releasably attaching the prosthesis to an implantation and inflation device, inflating the prosthesis using the implantation and inflation device for positioning the prosthesis in vivo, and after implantation, separating the prosthesis from the implantation and inflation device, thereby leaving the prosthesis at an implantation site.

6. A method according to claim 5, wherein the implantation and inflation device includes a tube for interfacing with the prosthesis in proximity of a sealing mechanism located at an end of the tube nearest the prosthesis.

7. A method according to claim 5, wherein placing the prosthesis includes using a sheath to maintain the prosthesis in a collapsed condition, placing the prosthesis into a space between rotator cuff tendons and the acromion using the implantation and inflation device, and withdrawing the sheath.

8. A method according to claim 1, wherein placing the prosthesis includes introducing the prosthesis through an arthroscopy port.

9. A method according to claim 1, further comprising sealing the prosthesis so that the sealed implanted prosthesis covers the humerus head during shoulder motion while remaining relatively fixed in relation to the acromion and/or the coracoid process.

10. A method according to claim 1, wherein inflating the prosthesis comprises filling the prosthesis to 60%-70% of the prosthesis maximum volume, so that the sealed implanted prosthesis permits shifting of prosthesis contents during movement of the shoulder.

11. A method according to claim 1, comprising inflating and sealing the prosthesis so that the sealed implanted prosthesis simulates the size or the shape of the naturally occurring bursa between the humerus and acromion in the shoulder.

12. A method according to claim 1, comprising inflating and sealing the prosthesis so that the sealed implanted prosthesis simulates the size or the shape of the naturally occurring bursa between the humerus and acromion process in the shoulder.

13. A method according to claim 1, comprising inflating and sealing the prosthesis so that the sealed implanted prosthesis simulates the size or the shape of the naturally occurring bursa between the humerus and coracoid process in the shoulder.

14. A method for implanting a prosthesis in a human shoulder, the method comprising:
providing an inflatable prosthesis;
placing the prosthesis proximal to, or in lieu of, a naturally occurring bursa between humerus and scapula in the shoulder;
inflating the prosthesis to a size or a shape of a naturally occurring bursa and to resemble characteristics of at least one of malleability and compressibility of the naturally occurring bursa; and
sealing the prosthesis so that the sealed implanted prosthesis covers the humerus head during shoulder motion while remaining relatively fixed in relation to the acromion and/or the coracoid process,
wherein the sealed implanted prosthesis is configured to: (1) reduce rubbing of soft tissues against other tissues of at least one of a humerus, the acromion or the coracoid process of the shoulder while permitting at least some movement of the soft tissues relative to the humerus, the acromion or the coracoid process, and (2) permit relatively unhindered or free shoulder movement.

15. A method according to claim 14, further comprising eluting at least one pharmaceutical agent from the prosthesis.

16. A method according to claim 14, wherein the soft tissues are tendons of a rotator cuff.

17. A method according to claim 14, wherein the prosthesis is a seamless balloon-like structure made from a biocompatible and/or a biodegradable synthetic material.

18. A method according to claim 14, further comprising releasably attaching the prosthesis to an implantation and inflation device, inflating the prosthesis using the implantation and inflation device for positioning the prosthesis in vivo, and after implantation, separating the prosthesis from the implantation and inflation device, thereby leaving the prosthesis at an implantation site.

19. A method according to claim 18, wherein the implantation and inflation device includes a tube for interfacing with the prosthesis in proximity of a sealing mechanism located at an end of the tube nearest the prosthesis.

20. A method according to claim 18, wherein placing the prosthesis includes using a sheath to maintain the prosthesis in a collapsed condition, placing the prosthesis into a space between rotator cuff tendons and the acromion using the implantation and inflation device, and withdrawing the sheath.

21. A method according to claim 14, wherein placing the prosthesis includes introducing the prosthesis through an arthroscopy port.

22. A method according to claim 14, wherein the prosthesis is deployed such that there is no interposition of the soft tissues between the implanted prosthesis and the acromion or the coracoid process, and the implanted prosthesis remains below the acromion during movement of the humerus.

23. A method according to claim 14, wherein inflating the prosthesis comprises filling the prosthesis to 60%-70% of the prosthesis maximum volume, so that the sealed implanted prosthesis permits shifting of prosthesis contents during movement of the shoulder.

24. A method according to claim 14, comprising inflating and sealing the prosthesis so that the sealed implanted prosthesis simulates the size or the shape of the naturally occurring bursa between the humerus and acromion in the shoulder.

25. A method according to claim 14, comprising inflating and sealing the prosthesis so that the sealed implanted prosthesis simulates the size or the shape of the naturally occurring bursa between the humerus and acromion process in the shoulder.

26. A method according to claim 14, comprising inflating and sealing the prosthesis so that the sealed implanted prosthesis simulates the size or the shape of the naturally occurring bursa between the humerus and coracoid process in the shoulder.

\* \* \* \* \*